US010583102B2

(12) United States Patent
Lutsenko et al.

(10) Patent No.: US 10,583,102 B2
(45) Date of Patent: Mar. 10, 2020

(54) TARGETING LIVER NUCLEAR RECEPTORS AS A TREATMENT FOR WILSON DISEASE

(71) Applicant: THE JOHNS HOPKINS UNIVERSITY, Baltimore, MD (US)

(72) Inventors: Svetlana Lutsenko, Baltimore, MD (US); James Hamilton, Reisterstown, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 15/517,197

(22) PCT Filed: Oct. 6, 2015

(86) PCT No.: PCT/US2015/054135
§ 371 (c)(1),
(2) Date: Sep. 18, 2017

(87) PCT Pub. No.: WO2016/057454
PCT Pub. Date: Apr. 14, 2016

(65) Prior Publication Data
US 2018/0036264 A1 Feb. 8, 2018

Related U.S. Application Data

(60) Provisional application No. 62/060,085, filed on Oct. 6, 2014.

(51) Int. Cl.
A61K 31/18 (2006.01)
A61K 33/30 (2006.01)
A61K 45/06 (2006.01)
A61K 31/132 (2006.01)
A61K 31/575 (2006.01)

(52) U.S. Cl.
CPC ............ *A61K 31/18* (2013.01); *A61K 31/132* (2013.01); *A61K 31/575* (2013.01); *A61K 33/30* (2013.01); *A61K 45/06* (2013.01)

(58) Field of Classification Search
CPC .. A61K 2300/00; A61K 45/06; A61K 31/575; A61K 31/13; A61K 31/155; A61K 31/167; A61K 31/4439; A61K 31/445; A61K 31/4985; A61K 31/55; A61K 33/30; A61K 38/26; A61K 31/18; A61K 31/132; A61K 48/005; A61K 31/542; A61K 31/4406; A61K 31/506; A61K 38/00; A61K 47/64; A61K 31/517; A61K 31/675; A61K 31/7056; A61K 31/7072; A61K 31/7076; A01K 2207/25; A01K 2227/105; A01K 2267/0362; A01K 67/027; C12N 2799/022; C12N 9/13
See application file for complete search history.

(56) References Cited

U.S. PATENT DOCUMENTS

| 6,316,503 | B1 | 11/2001 | Li et al. |
|---|---|---|---|
| 6,822,120 | B2 | 11/2004 | Becker et al. |
| 6,828,446 | B2 | 12/2004 | Chandrakumar et al. |
| 6,900,244 | B2 | 5/2005 | Van Camp et al. |
| 8,247,398 | B2 | 8/2012 | Goel |
| 2003/0086923 | A1 | 5/2003 | Sparrow et al. |
| 2003/0181420 | A1 | 9/2003 | Bayne et al. |
| 2003/0207898 | A1 | 11/2003 | Chandrakumar et al. |
| 2004/0048920 | A1 | 3/2004 | Becker et al. |
| 2004/0087632 | A1 | 6/2004 | Van Camp et al. |
| 2004/0110947 | A1 | 6/2004 | Chandrakumar et al. |
| 2005/0008011 | A1 | 1/2005 | Georgiou et al. |
| 2005/0009837 | A1 | 1/2005 | Forman |
| 2005/0036992 | A1 | 2/2005 | Saez et al. |
| 2005/0123580 | A1 | 6/2005 | Burris |
| 2005/0131014 | A1 | 6/2005 | Collini et al. |
| 2006/0030612 | A1 | 2/2006 | Steffan et al. |
| 2007/0207191 | A1 | 9/2007 | Kanzer et al. |

FOREIGN PATENT DOCUMENTS

| AU | 2007/227021 B2 | 3/2007 |
|---|---|---|
| EP | 1444979 B1 | 12/2009 |
| WO | 200141704 A2 | 6/2001 |
| WO | 2008036239 A2 | 3/2008 |

OTHER PUBLICATIONS

Hamilton, J. et al. "Treatment with the LXR agonist T0901317 ameliorates liver disease in ATP7b-I-(Wilson Disease) mice" Hepatology, Epub Oct. 1, 2014, vol. 60, No. 4 (Suppl) p. 275A, Abstract No. 153.*
Hamilton, et al. Hepatology, vol. 60, No. 4 [Suppl], AASLD Abstracts, "Treatment with the LXR agonist T0901317 ameliorates liver disease in Atp7b-/- (Wilson Disease) mice", Oct. 1, 2014. (Year: 2014).*
Riddell, "The LXR agonist TO901317 selectively lowers hippocampal Ab42 and improves memory in the TG2576 mouse model of Alzheimer's disease", Mol. Cell. Neurosci, 34, 2007, 621-628. (Year: 2007).*
Roberts. "Diagnosis and Treatment of Wilson Disease: An Update", Hepatology, vol. 47, No. 6, 2008, 2089-2111 (Year: 2008).*
Hamilton, J., et al., "Treatment with the LXR agonist T0901317 ameliorates liver disease in Atp7b-/- (Wilson Disease) mice" Hepatology, Epub. Oct. 1, 2014, vol. 60, No. 4 (Suppl) p. 275A, Abstract No. 153.
Lund, E., et al., "Liver X Receptor Agonists as Potential Therapeutic Agents for Dyslipidemia and Atherosclerosis", Arteriosclerosis, Thrombosis, and Vascular Biology, 2003, vol. 23, pp. 1169-1177.
(Continued)

Primary Examiner — Audrea B Coniglio
(74) Attorney, Agent, or Firm — Johns Hopkins Technology Ventures

(57) ABSTRACT

The present invention relates to the field of Wilson Disease. More specifically, the present invention provides methods and compositions useful for treating Wilson Disease by targeting liver nuclear receptors. In a specific embodiment, a method for treating Wilson Disease in a subject comprises the step of administering to the subject an effective amount of a liver X receptor (LXR) agonist.

19 Claims, 14 Drawing Sheets

(56) References Cited

OTHER PUBLICATIONS

Riddell, D., et al., "The LXR agonist TO901317 selectively lowers hippocampal Aβ42 and improves memory in the Tg2576 mouse model of Alzheimer's disease", Mol. Cell. Neurosci. 34 (2007) 621-628.

Roberts, E., et al., "Diagnosis and Treatment of Wilson Disease: An Update", Molecular and Cellular Neuroscience, 2007, vol. 34, pp. 621-628.

Menke, JG et al., A Novel Liver X Receptor Agonist Establishes Species Differences in the Regulation of Cholesterol 7a-Hydroxylase (CYP7a). Endocrinology 143:2548-58 (2002).

Joseph, SB et al., Synthetic LXR ligand inhibits the development of atherosclerosis in mice Sean B. Joseph*†, Elaine McKilligin†‡, Liming Pei*, Michael proc. Natl. Acad. Sci. USA 99:7604-09 (2002).

Fu, X et al., J. Biol. 27-Hydroxycholesterol Is an Endogenous Ligand for Liver X Receptor in Cholesterol-loaded Cells Chem. 276:38378-87 (2001).

Schultz, JR et al., Role of LXRs in control of lipogenesis Genes Dev. 14:2831-38 (2000).

Sparrow, C P. A Potent Synthetic LXR Agonist Is More Effective than Cholesterol Loading at Inducing ABCA1 mRNA and Stimulating Cholesterol Efflux. 20 et al., J. Biol. Chem. 277:10021-27 (2002).

Yang, C et al., Sterol Intermediates from Cholesterol Biosynthetic Pathway as Liver X Receptor Ligands. J. Biol. Chem., Manuscript M603781200 (Jul. 20, 2006).

Bramlett, KS et al., A Natural Product Ligand of the Oxysterol Receptor, Liver X Receptor. J. Pharmacol. Exp. Ther. 307:291-96 (2003).

Ondeyka, JG et al., Steroidal and Triterpenoidal Fungal Metabolites as Ligands of Liver X Receptors. J. Antibiot (Tokyo) 58:559-65 (2005).

Lutsenko, S. Atp7b-/- mice as a model for studies of Wilson's disease. 36 BIOCHEM. Soc. TRANS. 1233-38 (2008).

Buiakova, et al., A comprehensive method for extraction and quantitative analysis of sterols and secosteroids from human plasma. 8 HUM. MOL. GENET. 1665-71 (1999).

McDonald, et al. A comprehensive method for extraction and quantitative analysis of sterols and secosteroids from human plasma. (53(7) J. LIPID RES. 1399-I409 (20I2).

Roberts, E. A. et al., Diagnosis and treatment of Wilson disease: an update Hepatology, 2008, vol. 47, No. 6, pp. 2089-2111.

Riddell, D. R. et al., The LXR agonist T0901317 selectively lowers hippocampal AI3 42 and improves memory in the Tg2576 mouse model of Alzheimer's diseases Molecular and Cellular Neuroscience, 2007, vol. 34, pp. 621-628 See abstract.

Lund, E. G. et al., Liver X receptor agonists as potential therapeutic agents for dyslipidemia and atherosclerosis Arteriosclerosis, Thrombosis, and Vascular Biology, 2003, vol. 23, pp. 1169-1177.

Hamilton, J. P. et al., 'Treatment with the LXR agonist T0901317 ameliorates 1 liver disease in Atp7b-/-(Wilson Disease) mice Hepatology, Epub. Oct. 1, 2014, vol. 60, No. 4 (Suppl), p. 275A, Abstract No. 153.

Dalvi, et al. "Wilson's Disease: Etiology, Diagnosis, and Treatment." Disease-a-month. (2014). 60:450.

Tanzi et al. "The wilson disease gene is a copper transporting ATPase with Homology to the Menkes Disease Gene." Nat Genet. 1993. 5: 344-50.

Walshe et al. "Penicillamine, a New Oral Therapy for Wilson's Disease." 1956. Am. Jour. Med. 487-495.

Uhl et al. "Current Status in the Therapy of Liver Diseases." 2014. International Journal of Molecular Sciences. 15: 7500-7512.

\* cited by examiner

*p<0.005

TARGETING LIVER NUCLEAR RECEPTORS AS A TREATMENT FOR WILSON DISEASE

CROSS-REFERENCE TO RELATED APPLICATIONS

This application is a 35 U.S.C. § 371 U.S. national entry of International Application PCT/US2015/054135, having an international filing date of Oct. 6, 2015, which claims the benefit of U.S. Provisional Application No. 62/060,085, filed Oct. 6, 2014, the content of each of the aforementioned applications is herein incorporated by reference in their entirety.

STATEMENT OF GOVERNMENTAL INTEREST

This invention was made with government support under grant no. GM067166, awarded by the National Institutes of Health. The government has certain rights in the invention.

FIELD OF THE INVENTION

The present invention relates to the field of Wilson Disease. More specifically, the present invention provides methods and compositions useful for treating Wilson Disease by targeting liver nuclear receptors.

BACKGROUND OF THE INVENTION

Wilson Disease (WD) is an autosomal recessive, potentially fatal disease caused by mutations in the ATP-dependent copper transport protein, ATP7b. Over 300 mutations have been reported to cause disease, the incidence is estimated to be 1 in 30,000 births, and the disease typically presents in the first or second decade of life. Under normal conditions, ATP7b mediates the incorporation of 6 Copper (Cu) molecules into apoceruloplasmin, thereby forming ceruloplasmin. Ceruloplasmin is secreted into plasma, and excess Cu is deposited into lysosomes (again by ATP7b) for excretion into bile. The result of defective ATP7b function is accumulation of Cu in the liver, brain, cornea, and other organs. The mechanisms by which Cu accumulation causes liver injury have not yet been fully elucidated. Examination of liver specimens from patients with WD and Bedlington terriers with Cu overload revealed increased lipid peroxidation and mitochondrial Cu when compared to control liver. The classical dogma is that excess copper overwhelms the natural detoxifying functions of metallothionien and glutathione, leading to oxidative stress with resultant mitochondrial toxicity, inflammation which then precipitates fibrosis/cirrhosis. Counter current to this paradigm is that although the underlying genetic defect is similar and hepatic copper is always elevated in WD, disease manifestations vary, and either a hepatic, neurologic, or psychiatric phenotype may dominate. Hepatic presentations range from mild inflammation to hepatitis, cirrhosis, and acute liver failure. The molecular mechanisms behind this phenotypic variability are not known. In addition, the diagnosis and treatment of WD remain a challenge for clinicians. Currently, copper-chelation is available as a life-long therapy for WD. However, side effects (observed in more than 75% of patients) (4), poor compliance due to a very slow body response (6-46 months), and risk of neurologic decompensation complicate therapy (5). A better mechanistic understanding of WD is needed to improve both the diagnosis and treatment of this lethal disorder.

$ATP7b^{-/-}$ mice are an established model with which to investigate the mechanisms of pathogenesis in WD (6). Similar to the human disease, the $ATP7b^{-/-}$ mice accumulate copper in the liver, show lack of copper incorporation into ceruloplasmin, marked decrease of oxidase activity in plasma, and elevated copper in the urine. The mice achieve maximum concentrations of hepatic copper at 6 weeks, yet these mice do not have significant liver pathology until after 12-14 weeks (6). In previous studies of $ATP7b^{-/-}$ mice, transcriptional analysis was not consistent with widespread oxygen radical-mediated damage, rather, we found that lipid metabolism is the process most significantly affected by copper overload, even before significant histologic changes in the liver are present (7). Our bioinformatics studies indicated that the observed down-regulation of cholesterol biosynthesis is due to inhibition of the signaling events mediated by the nuclear liver X receptor (LXR). LXR is part of the superfamily of ligand dependent, nuclear receptor transcription factors. Oxidized derivatives of cholesterol (oxysterols) are the natural ligands of LXR, and have the ability to both agonize and antagonize LXR activation (8). LXRα (encoded by NR1H3) is highly expressed in the liver, macrophages, and other highly metabolic tissues, whereas LXRβ (NR1H2) is ubiquitously expressed (for detailed review see (9)). Upon ligand activation, LXRs form a heterodimer with the retinoid X-receptor (RXR), and play a critical role in modulation of lipid metabolism and inflammatory signaling (10). Furthermore, nuclear receptor agonists that affect cholesterol biosynthesis, transport, and bile acid metabolism have emerged as a potentially revolutionary breakthrough in the treatment of non-alcoholic fatty liver disease and cholestatic liver disease (11).

To further understand the relationship between elevated hepatic copper, down-regulated lipid metabolism, and liver disease, we correlated our genetic findings in $ATP7b^{-/-}$ mice with data from WD patients. We further investigated the impact of LXR activation in this mouse model of WD. Here we outline a previously unrecognized role for nuclear receptors in the pathogenesis of this complex human disease. These observations identify nuclear receptor activation as a potential target for novel therapeutic strategies in WD.

SUMMARY OF THE INVENTION

The present invention is based, at least in part, on the discovery that Wilson Disease can be treated by targeting liver nuclear receptors. In a specific embodiment, a method for treating Wilson Disease in a subject comprises the step of administering to the subject an effective amount of a liver nuclear receptor agonist.

Wilson Disease is a hepato-neurologic disorder caused by mutations in the gene ATP7B and accumulation of copper in tissues, predominantly in the liver. The disease is lethal, unless treated. Current life-long treatment involves copper chelation or copper replacement using Zn. Both procedures alleviate major symptoms but side effects are frequent and neurologic deterioration is often observed. Using Atp7b−/− mice (an animal model for Wilson' disease), we demonstrated that treatment of these animals (via addition to the diet) with the nuclear receptor agonist T0901317 markedly improves their liver function ameliorating major symptoms of the disease. T0901317 is a well-known agonist of LXR/RXR nuclear receptors that regulates lipid metabolism in the liver. Neither this compound nor any other activator of lipid metabolism has been previously employed for treatment of Wilson Disease symptoms. Targeting nuclear receptors in Wilson Disease represents an entirely new approach to treatment, which can potentially supplement, or be used as an alternative to treatment using copper chelators. Targeting nuclear receptor can be beneficial in a case of side effects (commonly observed in Wilson Disease) or during preparation for liver transplant.

In particular embodiments, the present invention provides an LXR agonist and a copper chelator for use in a method of treating a patient having Wilson Disease. In a specific embodiment, the LXR agonist is a natural oxysterol, a synthetic oxysterol, a synthetic nonoxysterol or a natural nonoxysterol. In more specific embodiment, the LXR agonist is 20(S) hydroxycholesterol, 22(R) hydroxycholesterol, 24(S) hydroxycholesterol, 25-hydroxycholesterol, 24(S), 25 epoxycholesterol, 27-hydroxycholesterol, N,N-dimethyl-3.beta.-hydroxycholenamide, N-(2,2,2-trifluoroethyl)-N-{4-[2,2,2-trifluoro-1-hydroxy-1-(trifluorometh-yl)ethyl]phenyl}benzene sulfonamide, [3-(3-(2-chloro-trifluoromethylbenzyl-2,2-diphenylethylamino)propoxy) phen-ylacetic acid], N-methyl-N-[4-(2,2,2-trifluoro-1-hydroxy-1-trifluoromethyl-1-ethyl)-pheny-1]-benzenesulfonamide, 4,5-dihydro-1-(3-(3-(3-trifluoromethyl-7-propyl-benzisoxazol-6-yloxy)propyl)-2,6-pyrimidinedione, 3-chloro-4-(3-(7-propyl-3-trifluoromethyl-6-(4,5)-isoxazolyl)propylthio)-phenyl acetic acid, acetyl-podocarpic dimer, paxilline, desmosterol, or stigmasterol. In particular embodiments, the copper chelator is penicillamine, bathocuproine sulfonate, sodium diethyl-dithiocarbamate, trientine hydrochloride, dimercaprol or zinc acetate.

The present invention also provides a method for treating a patient suffering from Wilson Disease comprising the step of administering to the patient an effective amount of a liver X receptor (LXR) agonist. The LXR agonist can be a natural oxysterol, a synthetic oxysterol, a synthetic nonoxysterol or a natural nonoxysterol. In particular embodiments, the LXR agonist is 20(S) hydroxycholesterol, 22(R) hydroxycholesterol, 24(S) hydroxycholesterol, 25-hydroxycholesterol, 24(S), 25 epoxycholesterol, 27-hydroxycholesterol, N,N-dimethyl-3.beta.-hydroxycholenamide, N-(2,2,2-trifluoro-ethyl)-N-{4-[2,2,2-trifluoro-1-hydroxy-1-(trifluorometh-yl)ethyl]phenyl}benzene sulfonamide, [3-(3-(2-chloro-trifluoromethylbenzyl-2,2-diphenylethylamino)propoxy) phen-ylacetic acid], N-methyl-N-[4-(2,2,2-trifluoro-1-hydroxy-1-trifluoromethyl-1-ethyl)-pheny-1]-benzenesulfonamide, 4,5-dihydro-1-(3-(3-trifluoromethyl-7-propyl-benzisoxazol-6-yloxy)propyl)-2,6-pyrimidinedione, 3-chloro-4-(3-(7-propyl-3-trifluoromethyl-6-(4,5)-isoxazolyl)propylthio)-phenyl acetic acid, acetyl-podocarpic dimer, paxilline, desmosterol, or stigmasterol.

In specific embodiments, the LXR agonist is N-(2,2,2-trifluoroethyl)-N-[4-(2,2,2-trifluoro-1-hydroxy-1-trifluoromethy-1-1-ethyl)-phenyl]-benzenesulfonamide. In certain embodiments, the LXR agonist is 22(R)-hydroxycholesterol, 24(S)-hydroxycholesterol, 27-hydroxycholesterol, or cholestenoic acid. In a specific embodiment, the LXR agonist is hypocholamide, T0901317, GW3965, or N,N-dimethyl-3beta-hydroxy-cholenamide (DMHCA).

The present invention also provides compositions comprising an LXR agonist. In certain embodiments, a pharmaceutical composition comprises an LXR agonist and a copper chelator. The copper chelator can be penicillamine, bathocuproine sulfonate, sodium diethyldithiocarbamate, trientine hydrochloride, or dimercaprol. In specific embodiments, the copper chelator is penicillamine or tientine hydrochloride.

The present invention also provides pharmaceutical compositions comprising an LXR agonist and a metallothionein inducer. In a specific embodiment, the metallothionein inducer is a zinc salt. In a more specific embodiment, the zinc salt is zinc acetate. In another embodiment, a pharmaceutical composition comprises an LXR agonist and zinc acetate.

In a further embodiment, the present invention provides a pharmaceutical composition comprising an LXR agonist, a copper chelator and a metallothionein inducer. In a specific embodiment, a pharmaceutical composition comprises an LXR agonist, a copper chelator and zinc acetate. As described herein, the composition can comprise a dose of a chelator and/or metallothionein inducer that is lower than typically prescribed for such drugs alone.

BRIEF DESCRIPTION OF THE FIGURES

FIG. 1A shows the pathway analysis and identifies LXR/RXR (large grey oval) as a key pathway affected. Upregulated genes are green and downregulated genes are red. Arrows indicate the targets of the signaling pathway activation. The graph in FIG. 1B demonstrates that LXR/RXR activation is most significantly down-regulated set of genes. The chart in FIG. 1C indicates that the genes governing lipid and carbohydrate metabolism are the most commonly affected biological processes.

FIG. 2A shows the relative expression of mRNA of genes associated with the LXR/RXR pathway. The concentrations of several oxysterols are shown in FIG. 2B. 7($\alpha,\beta$) OHC and 5/6b EC were both significantly reduced in the KO mice. The RXR, LXR alpha, and LXR Beta protein levels from the nuclear fractions of whole liver lysates are shown in FIG. 2C. RXR was significantly reduced in the KO mice. (*$p<0.05$)

Severely inflamed livers had cytomegaly (large black arrow), inflammatory infiltrates (small black arrow), and binucleate hepatocytes (white arrow). These changes were significantly improved in the treated KO mice.

Figure 6:
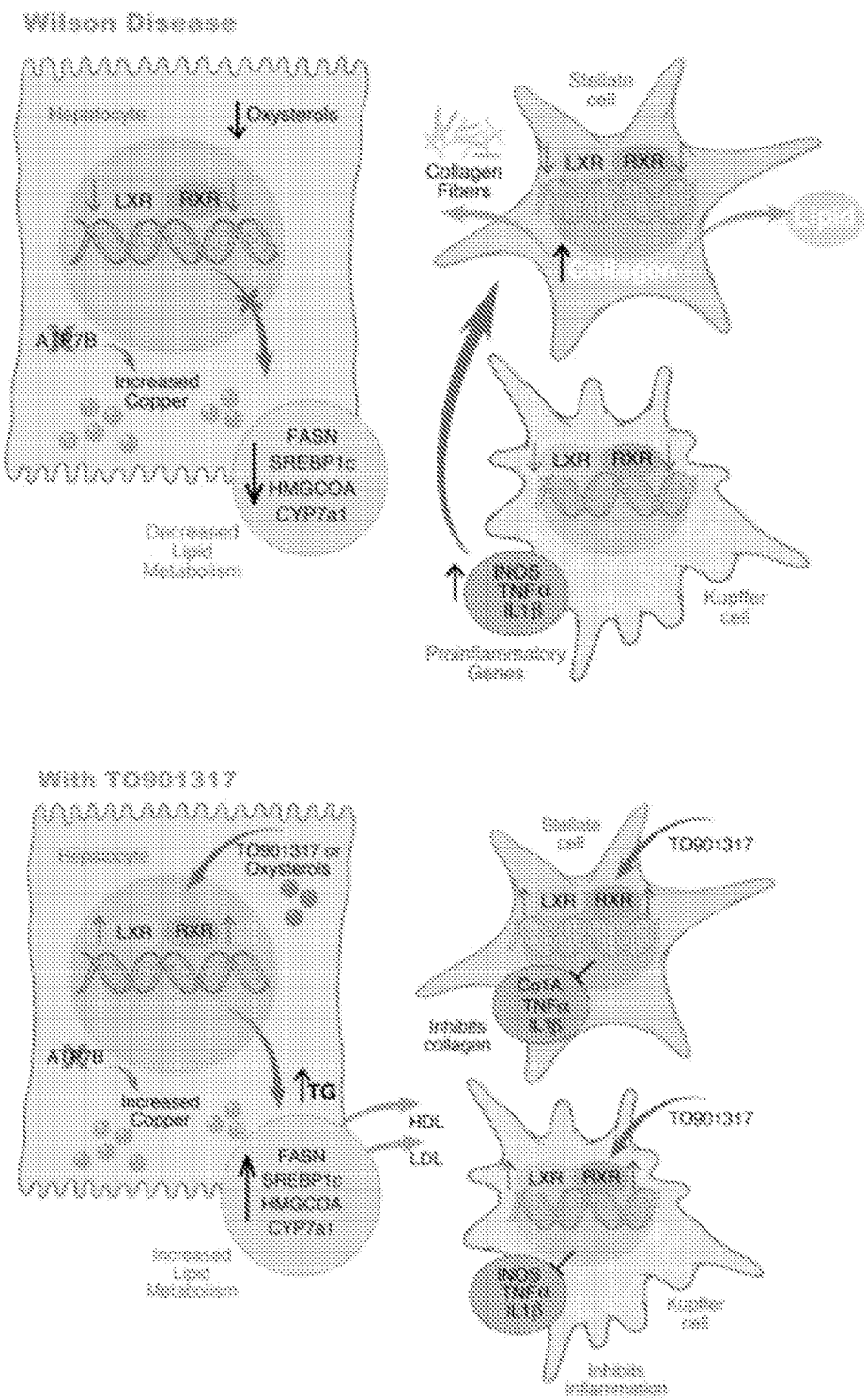

FIG. 6. Schematic of proposed LXR/RXR physiology in WD. In the WD mouse, there is increased hepatic copper, reduced levels of oxysterols, reduced LXR/RXR activity, and reduced lipid metabolism. The copper induces cellular stress, which stimulates Kupffer cells to produce pro-inflammatory cytokines, which in turn activate stellate cells to synthesize collagen. LXR/RXR inactivation in macrophages prevents transrepression of pro-inflammatory genes (top panel). Treatment with the synthetic LXR ligand TO901317, stimulates LXR/RXR activation, leading to increased lipid metabolism, increased hepatic triglycerides, while at the same time negatively regulating pro-inflammatory and pro-fibrotic gene expression in macrophages and stellate cells, respectively (bottom panel).

Figure 7:
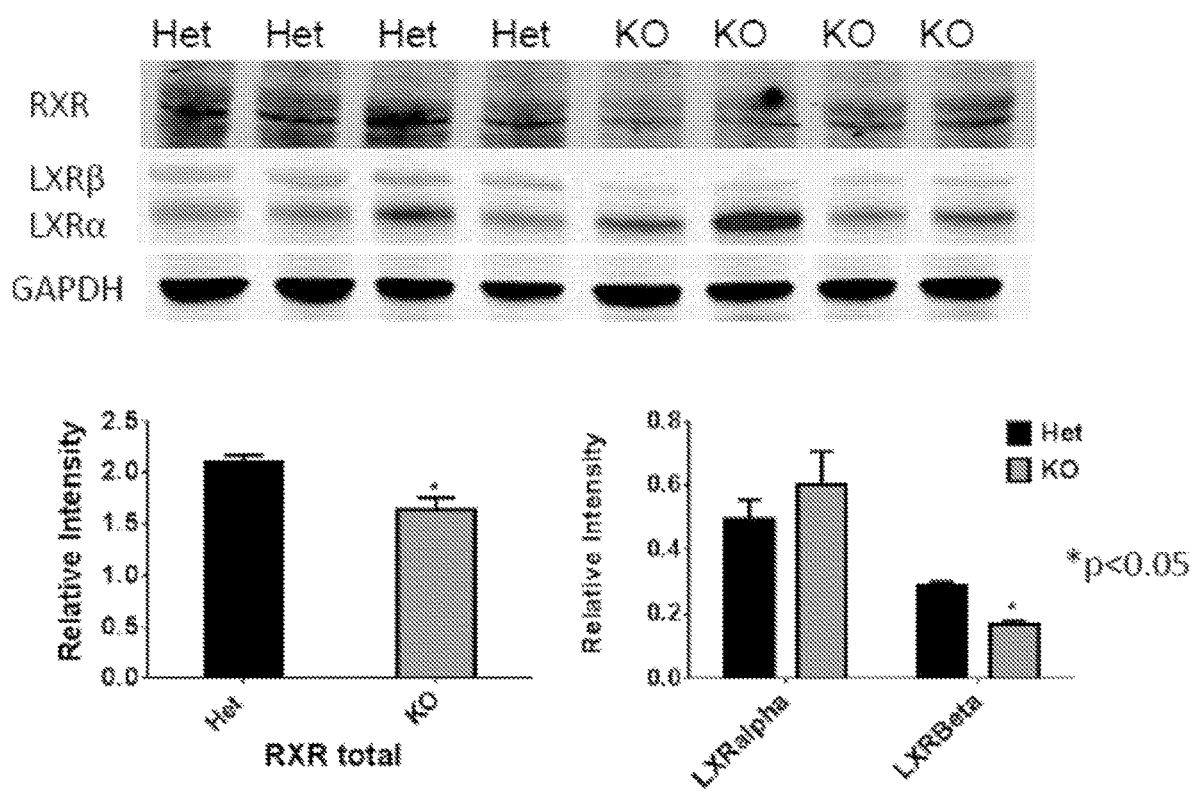

FIG. 7. Cytoplasmic levels of RXR, LXR Alpha, and LXR Beta from ATP7b knockout out and heterozygote control mice. The top panel shows the Western blot images, and the bottom panels are the image intensities. There was a reduced cytoplasmic amount of RXR and LXR Beta in the ATP7b knockout mice.

Figure 8A:
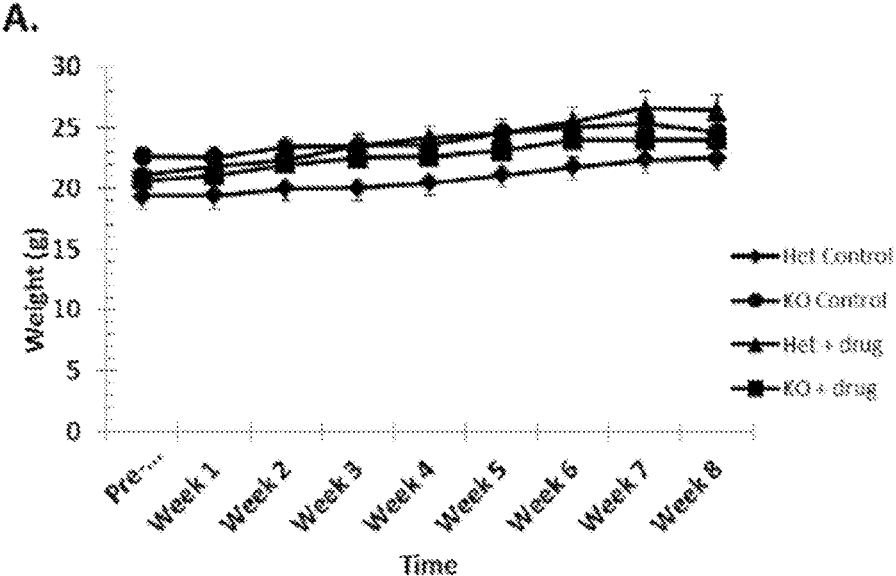
Figure 8B:
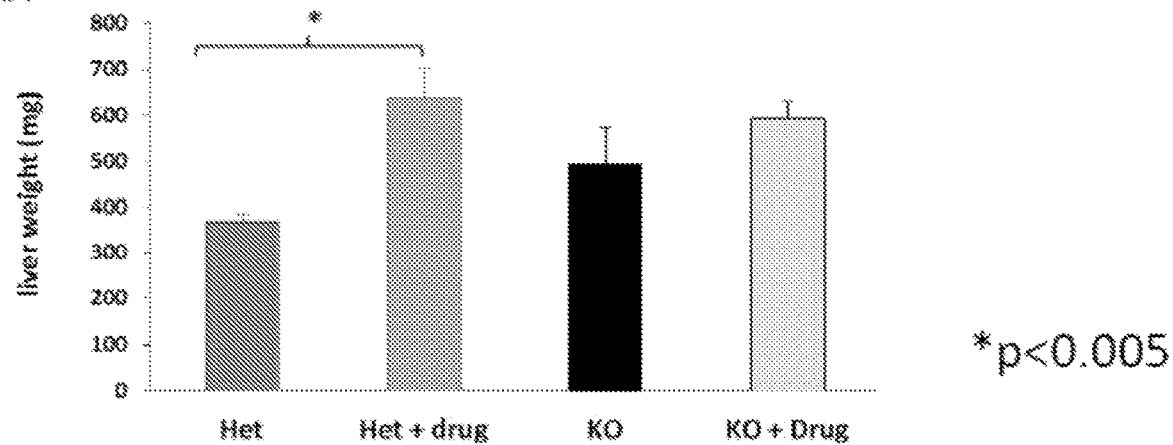

FIG. 8A-8B. FIG. 8A: animal weights of mice during treatment. FIG. 8B: liver weights at end of treatment ($*p<0.005$).

Figure 9:
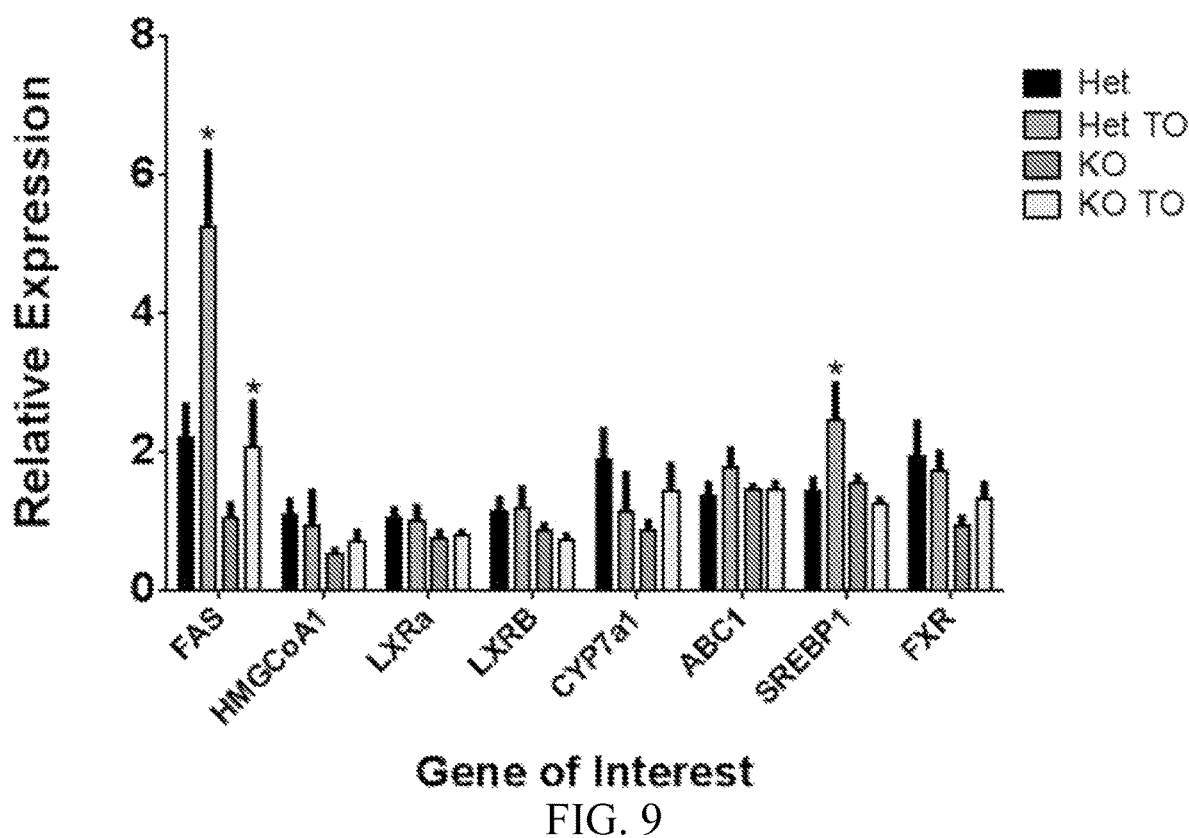

FIG. 9. The effect of LXR agonist on genes under control of LXR/RXR signaling pathway. The asterisk indicates comparison between treated and untreated mice of the same genotype ($p<0.05$).

Figure 10:
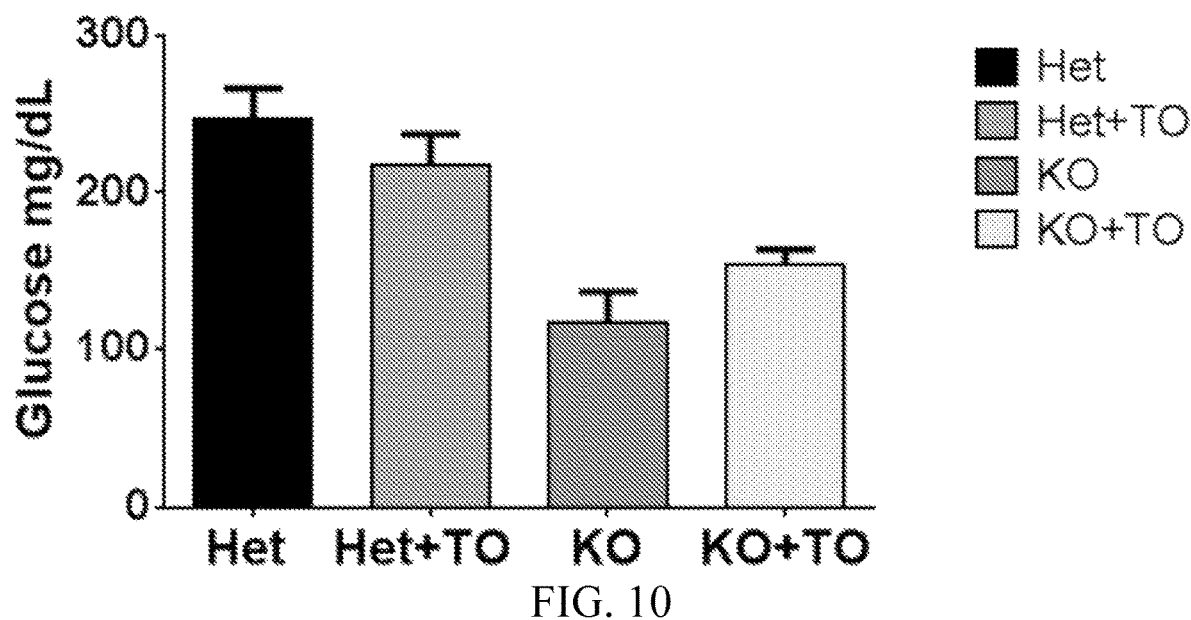

FIG. 10. Effects of LXR agonist on serum glucose in ATP7b heterozygote (HET) and knockout (KO) mice.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

"Liver X receptor" or "LXR" refers to both LXRα and LXRβ, and variants, isoforms, and active fragments thereof.

As used herein, the term "effective amount" refers to the amount of an agent (e.g., a prophylactic or therapeutic agent) which is sufficient to cause the desired effect in the particular context, such as to agonize LXR activity, stimulate and/or enhance LXR activity, induce/enhance LXR expression/activity, induce an LXR-mediated signaling, prevent, reduce or ameliorate the severity, duration and/or progression of a disease or condition or one or more symptoms thereof (e.g., Wilson Disease), ameliorate one or more symptoms of a disease or condition, prevent the advancement of a disease or condition, cause regression of a disease or condition, prevent the recurrence, development, or onset of a disease or condition or one or more symptoms thereof, or enhance or improve the prophylactic or therapeutic effect (s) of another therapy (e.g., prophylactic or therapeutic agent).

The term "LXR agonist" refers to an agent capable of activating, enhancing, increasing, or otherwise stimulating one or more functions of the target LXR. An agonist of LXR may induce any LXR activity, for example LXR-mediated signalling, either directly or indirectly. A LXR agonist, as used herein, may but is not required to bind an LXR, and may or may not interact directly with the LXR. An LXR agonist can specifically agonize LXRα, LXRβ or both. An LXR agonist may affect other receptors/pathways in addition to agonizing LXR.

The terms "specifically binds to," "specific for," and related grammatical variants refer to that binding which occurs between such paired species as antibody/antigen, enzyme/substrate, receptor/agonist, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M.

Optional" or "optionally" means that the subsequently described event or circumstance can or cannot occur, and that the description includes instances where the event or circumstance occurs and instances where it does not.

As used herein, the terms "patient", "subject" and "subjects" refer to an animal, preferably a mammal including, but not limited to, a non-primate (e.g., a cow, pig, horse, cat, dog, rat, and mouse) and a non-human primates (e.g., a monkey such as a cynomolgous monkey), and more preferably a human. In a specific embodiment, the subject is a human.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

II. LXR Agonists

LXR agonists useful in the present invention include natural oxysterols, synthetic oxysterols, synthetic nonoxysterols, and natural nonoxysterols. Exemplary natural oxysterols include 20(S) hydroxycholesterol, 22(R) hydroxycholesterol, 24(S) hydroxycholesterol, 25-hydroxycholesterol, 24(S), 25 epoxycholesterol, and 27-hydroxycholesterol. Exemplary synthetic oxysterols include N,N-dimethyl-3.beta.-hydroxycholenamide (DMHCA). Exemplary synthetic nonoxysterols include N-(2,2,2-trifluoroethyl)-N-{4-[2,2,2-trifluoro-1-hydroxy-1-(trifluorometh-yl)ethyl] phenyl}benzene sulfonamide (TO901317; Tularik 0901317), [3-(3-(2-chloro-trifluoromethylbenzyl-2,2-diphenylethylamino)propoxy)phen-ylacetic acid] (GW3965), N-methyl-N-[4-(2,2,2-trifluoro-1-hydroxy-1-trifluoromethyl-1-ethyl)-pheny-1]-benzenesulfonamide (TO314407), 4,5-dihydro-1-(3-(3-trifluoromethyl-7-propyl-benzisoxazol-6-yloxy)propyl)-2,6-pyrimidinedione, 3-chloro-4-(3-(7-propyl-3-trifluoromethyl-6-(4,5)-isoxazolyl)propylthio)-phenyl acetic acid (F.sub.3-MethylAA), and acetyl-podocarpic dimer. Exemplary natural nonoxysterols include paxilline, desmosterol, and stigmasterol.

Other useful LXR agonists are disclosed, for example, in Published U.S. Patent Application Nos. 2006/0030612, 2005/0131014, 2005/0036992, 2005/0080111, 2003/0181420, 2003/0086923, 2003/0207898, 2004/0110947, 2004/0087632, 2005/0009837, 2004/0048920, and 2005/0123580; U.S. Pat. Nos. 6,316,503, 6,828,446, 6,822,120, and 6,900,244; WO2008036239; WO2001/41704; Menke J G et al., Endocrinology 143:2548-58 (2002); Joseph S B et al., Proc. Natl. Acad. Sci. USA 99:7604-09 (2002); Fu X et al., J. Biol. Chem. 276:38378-87 (2001); Schultz J R et al., Genes Dev. 14:2831-38 (2000); Sparrow C P et al., J. Biol. Chem. 277:10021-27 (2002); Yang C et al., J. Biol. Chem., Manuscript M603781200 (Jul. 20, 2006); Bramlett K S et al., J. Pharmacol. Exp. Ther. 307:291-96 (2003); Ondeyka J G et al., J. Antibiot (Tokyo) 58:559-65 (2005).

Oxysterols, the oxygenated derivatives of cholesterol, such as 22(R)-hydroxycholesterol, 24(S)-hydroxycholesterol, 27-hydroxycholesterol, and cholestenoic acid, are the natural ligands for LXR. Examples of LXR agonists specifically include, but are not limited to, hypocholamide, T0901317, GW3965, or N,N-dimethyl-3beta-hydroxycholenamide (DMHCA).

III. Screening Methods

The present invention provides methods for screening for LXR agonists. Such methods include the use of the present inventors' mouse model of WD. In particular embodiments, a method of screening for LXR agonists or otherwise evaluating candidate LXR agonists comprises the steps of administering a test agent or candidate LXR agonist to a mouse model of WD and evaluating the effects of the test agent on one or more symptoms of WD exhibited by the mouse model. Measurable outcomes are described herein and can include, but are not limited to, activation of lipid metabolism, reduction of inflammation, and the like. In certain embodiments, the mouse model of WD comprises an ATP7b knockout (ATP-/-). See Lutsenko, S. 36 BIOCHEM. Soc. TRANS. 1233-38 (2008); and Buiakova et al., 8 HUM. MOL. GENET. 1665-71 (1999).

IV. Pharmaceutical Compositions

The present invention also provides pharmaceutical compositions comprising an LXR agonist. The compositions can also comprise a WD therapeutic including, but not limited to, penicillamine, trientine and/or zinc acetate. Penicillamine (Cuprimine, Depen) is a copper chelating agent. Penicillamine can cause serious side effects, including skin problems, bone marrow suppression and worsening of neurological symptoms. Trientine (Syprine) works much like penicillamine, but tends to cause fewer side effects. Still, there is a risk that neurological symptoms can worsen when taking trientine, though it's thought to be a lower risk than is penicillamine. Zinc acetate (Galzin) prevents a patient's body from absorbing copper from the food the patient has eaten. Zinc acetate can cause an upset stomach.

In particular embodiments, a composition comprises an LXR agonist and a copper chelator. The chelator can be, but is not limited to, penicillamine (e.g., Cuprimine or Depen) or trientine (e.g., Syprine). In more particular embodiments, the composition can comprise a lower dose of a chelator than is currently prescribed for administration of the chelator alone. In other embodiments, a composition comprises an LXR agonist and a metallothionein inducer including, but not limited to, zinc acetate (Galzin) (zinc acetate can also act as a chelator). Embodiments comprising zinc can include mineral zinc; mineral zinc complexes or zinc salts, e.g. zinc oxide; zinc pyrithione; zinc acetate; zinc gluconate; zinc picolinate; zinc sulfate; zinc citrate; zinc glycerate; zinc monomethionine; zinc aspartate; zinc lactate, zinc malate; zinc tartrate; orotate and zinc amino acid chelates. The composition can comprise a lower dose of the metallothionein inducer than is currently prescribed for administration of the metallothionein alone. Such compositions having a lower dose of a chelator and/or metallothionein inducer are expected to have lower side effects in patients than use of currently prescribed amounts for chelators alone or metallothionein inducers alone. In specific embodiments, a composition comprises an LXR agonist and zinc acetate.

For example, the composition comprising (a) an LXR agonist and (b) either a chelator or a metallothionein inducer can comprise an amount of chelator/metallothionein inducer that is 1-99% of the typical dose of a chelator/metallothionein inducer. In specific embodiments, the chelator/metallothionein inducer can comprise 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 83%, 84%, 85%, 86%, 87%, 88%, 89%, 90%, 91%, 92%, 93%, 94%, 95%, 96%, 97%, 98%, or 99% of the typical dose of a chelator/metallothionein inducer prescribed as the sole therapy for Wilson Disease. The foregoing can also be expressed in terms of a range of any of the percentages listed above (e.g., 10-80%, 20-70%, 25-75% and the like) or a threshold (e.g., less than 80%, less than 50%, no more than 90%, and the like). Cuprimine and Depen (pencillamine) is prescribed in a range of about 500-1500 mg/day. Syprine (trientine hydrochloride) is prescribed as an initial dose of 500-700 mg/day for pediatric patients and 750-1250 mg/day for adults given in divided doses two, three, or four times daily. This may be increased to a maximum of 2000 mg/day for adults or 1500 mg/day for pediatric patients age 12 or under. Galzin (zinc acetate) is prescribed for 50 mg three times for adults. In the present invention, the dosage of such drugs can be reduced by a percentage or range of percentages described above.

The present invention also provides compositions comprising an LXR agonist, a chelator and a metallothionein inducer. Such compositions can comprise a lower dose of a chelator and metallothionein than is typically prescribed.

Without further elaboration, it is believed that one skilled in the art, using the preceding description, can utilize the present invention to the fullest extent. The following examples are illustrative only, and not limiting of the remainder of the disclosure in any way whatsoever.

Examples

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Wilson disease (WD) is a hepatoneurologic disorder caused by mutations in the copper-transporter ATP7B. Copper accumulation in the liver is a hallmark of WD. Current therapy is based on copper chelation, which decreases the manifestations of liver disease, but often worsens neurologic symptoms. We demonstrate that in Atp7b$^{-/-}$ mice, an animal model of WD, liver function can be significantly improved without copper chelation. Analysis of transcriptional and metabolic changes in samples from WD patients and Atp7b$^{-/-}$ mice identified disregulation of nuclear receptors (NR), especially the LXR/RXR heterodimer, as an important event in WD pathogenesis. Treating Atp7b$^{-/-}$ mice with the LXR agonist T0901317 ameliorated disease manifestations despite significant copper overload. Genetic markers of liver fibrosis and inflammatory cytokines were significantly decreased, lipid profiles normalized and liver function and histology was improved. In conclusion, the results indicate that modulation of nuclear receptor activity could be an independent or supplementary approach to improving liver function in WD.

Introduction

Wilson Disease (WD) is a potentially fatal disease caused by mutations in the ATP-dependent copper transport protein, ATP7B. In hepatocytes, ATP7B facilitates copper delivery to the copper-dependent ferroxidase, ceruloplasmin, which undergoes functional maturation in a secretory pathway. ATP7B also maintains cytosolic copper at a non-toxic level by sequestering excess copper in vesicles for subsequent export into bile. WD causing mutations disrupt ATP7B function, resulting in accumulation of Cu in tissues, especially liver. The disease manifestations are highly variable, indicative of modifying factors, and pose significant challenges for diagnosis and treatment. Copper chelation is the major and largely successful therapy for WD. However, frequent side effects, poor compliance, neurologic decompensation, and cost complicate therapy. Development of additional or supplementary approaches requires a better understanding of the pathogenesis of WD. Atp7b$^{-/-}$ mice are established model for studies of WD. These animals recapitulate the major manifestations of WD, including hepatic copper overload, loss of ceruloplasmin activity, elevated urine copper, and liver disease. In both mice and humans, the severity of pathology is not proportional to the amount of hepatic copper, further indicating a modifying influence of metabolic and/or environmental factors. A significant role for metabolism is also suggested by discordant clinical disease in monozygotic WD twins with different nutritional histories.

Our previous studies identified lipid metabolism, especially cholesterol biosynthesis, as the major metabolic pathway inhibited in response to hepatic copper accumulation in Atp7b$^{-/-}$ mice prior to the onset of hepatitis. Similar findings in LEC rats prompted human studies that described lower total cholesterol in WD patients compared to patients with comparable liver disease. Diminished levels/activity of HMG-CoA reductase is observed in all three species. Here, we expand upon this work to identify the molecular basis of lipid dysregulation in WD. Our study provides direct evidence that abnormally reduced function of nuclear receptors involved in the reciprocal regulation of lipid metabolism and inflammatory response is the major event that triggers the onset and progression of liver pathology in WD. Furthermore, we demonstrate that upregulation of nuclear receptor function can ameliorate the disease even in the presence of high copper. These findings provide a foundation to develop novel treatments for WD.

Materials and Methods

Human Studies.

In accordance with Declaration of Helsinki and Institutional Review Board (U. Leipzig Reg. #236-2006; U. Heidelberg Reg. #346/2005) approved consent, WD patients underwent liver transplantation for acute or chronic liver failure. Control specimens were obtained from patients who underwent liver resections for other clinical reasons. Liver sections were snap frozen in liquid nitrogen and stored. Total RNA was isolated using TRIZOL reagent (Invitrogen, Grand Island, N.Y.) followed by RNeasy cleanup procedure (Qiagen, Valencia, Calif.). The integrity of isolated RNA was verified by ethidium bromide staining and by optical densities (OD) ratio (OD260 nm/280 nm>1.8). A total of 16 liver RNA samples (8 biological replicates for control liver and 8 for WD patients) were examined for RNA integrity and concentration on an Agilent 2100 Bioanalyzer (Agilent Technologies, Palo Alto, Calif., USA) using the RNA 6.000 LabChip Kit (Agilent Technologies) according to the manufacturer's instructions.

Affymetrix GeneChip analysis was conducted at the microarray core facility of the University of Leipzig). 2 µg of total RNA were used to prepare double-stranded cDNA (Superscript II, Life Technologies, Gaithersburg, Md.) primed with oligo-dT containing an T7 RNA polymerase promoter site (Genset SA, Paris, France). cDNA was purified by phenol-chloroform extraction before in vitro transcription using the IVT labeling kit (Affymetrix, Santa Clara, Calif., USA) to synthesize cRNA. After the in vitro transcription, unincorporated nucleotides were removed using the RNeasy kit (QIAGEN). The cRNA was fragmented and hybridized to two different (technical replicates) Human Genome U133 Plus 2.0 (Arrays Affymetrix). The washing and staining of the probe array was performed according to the manufacturer's instructions. The array was scanned with a third generation Affymetrix GeneChipScanner 3000.

Image processing and analysis were performed using Affymetrix MAS 5.0 software. The resulting intensities and coordinate information were saved in a CEL file format and then subjected to global scaling with an average target intensity of 350 to allow for direct comparison of hybridization values from different targets. Scaled results for each sample were saved as CHP files and these data were used to evaluate overall chip performance. The analysis indicated that the parameters describing the quality of RNA, hybridization, and detection were all within acceptable range.

The associations between altered genes or pathways were evaluated using the Ingenuity Pathways Analysis software. Affymetrix identifiers of the differentially expressed genes (the fold-change of 1.5 or higher) and their corresponding expression values were loaded into the software and mapped to its corresponding gene object (so-called focus genes) in the Ingenuity Pathways Knowledge Base. The significance of the associations between the data set and the canonical pathway and functional annotations was calculated in two ways. First, the number of genes from the data set mapping to a pathway was divided by the number of all known genes ascribed to the pathway. Second, the left-tailed Fischer's exact test was used to calculate related p-values and distinguish those functional/pathway annotations which had more Focus Genes than expected by chance. The networks of the focus genes were algorithmically generated based on their connectivity.

Animal Studies.

ATP7b knockout (ATP7b$^{-/-}$) and heterozygote (ATP7b$^{+/-}$) mice were generated as previously prescribed (Buiakova et al., 8(9) HUM. MOL. GENETICS 1665-71 (1999). T0901317 (Cayman Chemical, Ann Arbor, Mich.) powder was mixed with Teklad 2018 powdered chow (Harlan, Madison Wis.) and fed to animals aged 6-7 weeks old at a dose of 50 mg/kg/day, thrice weekly. After 8 weeks, animals were sacrificed. The animals were housed at the Johns Hopkins University School of Medicine (JHUSOM) Animal Care Facility and protocols designed according to National Institutes of Health (USA) guidelines. Normal pellet chow was fed to the mice on days they were not receiving the drug. Animals were weighed weekly. At the time of sacrifice, trunk blood and livers were harvested. The Institutional Animal Care and Use Committee (IACUC) of JHUSOM approved the above experimental protocols.

Serum Biochemical Analysis.

Animals were fasted overnight before sacrifice. Whole blood was collected from the aorta and vena cava in amber Microtainer tubes (Becton Dickinson, Franklin Lakes, N.J.), and serum was separated after centrifugation at 5000 rpm for 10 minutes. Liver biochemistries and lipid panels were performed in the Molecular and Comparative Pathobiology Core Laboratory of JHUSOM.

Quantitative RT-PCR.

Sections of mouse liver were immersed in RNAlater, homogenized, and frozen at −80° C. RNA was isolated with TRIzol via the manufacturer's instructions, then transcribed into cDNA using the SuperScript III first strand synthesis system (Invitrogen). RNA quantity was determined by an ND-1000 spectrophotometer (NanoDrop, Wilmington, Del.). Samples were run in triplicate and performed on a 7900 HT machine (Applied Biosystems) and analyzed with the SDS 2.4.1 software. GAPDH served as the control to which gene of interest expression was normalized.

Quantitative RT-PCR for ABC1, HmGCoA1, CYP71a, FASN, LXRα (NR1H3), LXRβ (NR1H2), RXRα (NR2B2), SREBP1, FXR, TIMP1, COL1a, and GAPDHwas performed with sequence-specific primers and probes using TaqMan gene expression assays (Applied Biosystems, Foster City, Calif.).

Immunoblotting.

Antibodies were purchased from Santa Cruz Biotechnology, Inc. (Dallas), Cell signaling (Beverly, Mass.), or Abcam (Cambridge, Mass.). Cytoplasmic and nuclear protein was extracted using the NE-PER™ kit (Thermo Scientific). Immunoblotting for LXRα (SC-1202), LXRβ (SC-1203), RXR (SC-831), p38 MAPK (CS-8690S), P-p38 MAPK (CS-4511S), SAPK/JNK (CS-9252S), P-SAPK/JNK (CS-9251S), ERK 1/2 (CS-9102S), P-ERK 1/2 (CS-9101S), and GAPDH (ab8245) was performed as previously described. Densitometry was performed using Image J software (National Institutes of Health, Bethesda).

Histology.

Sections of mouse liver were covered in OCT and snap frozen in liquid nitrogen. Sections were then cut and stained with hematoxylin and eosin. De-identified samples were analyzed for the presence of inflammation by an expert in veterinary pathology (D.H.). Inflammation was scored as follows: none, 0; mild, 1; moderate, 2; and severe, 3. Severely inflamed livers had karyomegaly, cytomegaly, binucleate hepatocytes, intranuclear vacuoles, multiple nuclei, and inflammatory cell infiltrates.

Hepatic Copper Measurements.

Hepatic copper levels were measured by polarized atomic absorption spectroscopy as previously described. Briefly, 50-100 mg of liver was dissolved in 2 ml of $HNO_3$ at 90° C. Copper levels were determined using a Hitachi Z-8279 spectrophotometer. Samples were compared to freshly prepared standards.

Hepatic Triglyceride Measurements.

The triglyceride colorimetric assay kit (Cayman Chemical, Ann Arbor, Mich.) was used for measuring hepatic triglyceride content using the provided protocol. 120-160 mg of liver tissue was homogenized and samples were assayed in triplicate. Absorbance at 540 nm was detected on an Envision plate reader (Perkin-Elmer). Triglyceride concentrations were calculated using a standard curve, then normalized to the volume of homogenate and the mass of the liver tissue.

Hepatic Oxysterol Measurements.

Oxysterols were extracted and measured using the protocol described by McDonald et al. (53(7) J. LIPID RES. 1399-1409 (2012)). 1 mg of liver tissue was macerated, solubilized with methylene chloride and methanol, saponified with 10N KOH, and purified with hexane and aminopropyl SPE cartridges (Biotage, Uppsula, Sweden). Mass spectrometry was carried out using LC/MS on a triple quadrupole mass spectrometer (AB SCIEX 5500, Framingham, Mass.) in multiple reaction monitoring (MRM) mode. The HPLC column used for these analyses was 2×150 mm 2.6 mm particle size Kinetix column (Phenomenex Torrance, Calif.) at a flow rate of 2.5 ml/min. Quantitation was performed by establishing a linear relationship between measured amounts of the analytical standards combined with the internal standard cocktail. This regression line was applied to the measured peak areas for analytes in the extracted samples to determine measured quantities present in each sample. The numbers were normalized to the wet weight of the tissue extracted and reported as picograms of analyte/wet weight tissue.

Statistical Analysis.

Data are presented as the mean and the standard error (SE) of the mean. The data were analyzed with the two-tailed student's t-test, and p values less than 0.05 were considered significant.

Results

Figure 1A:
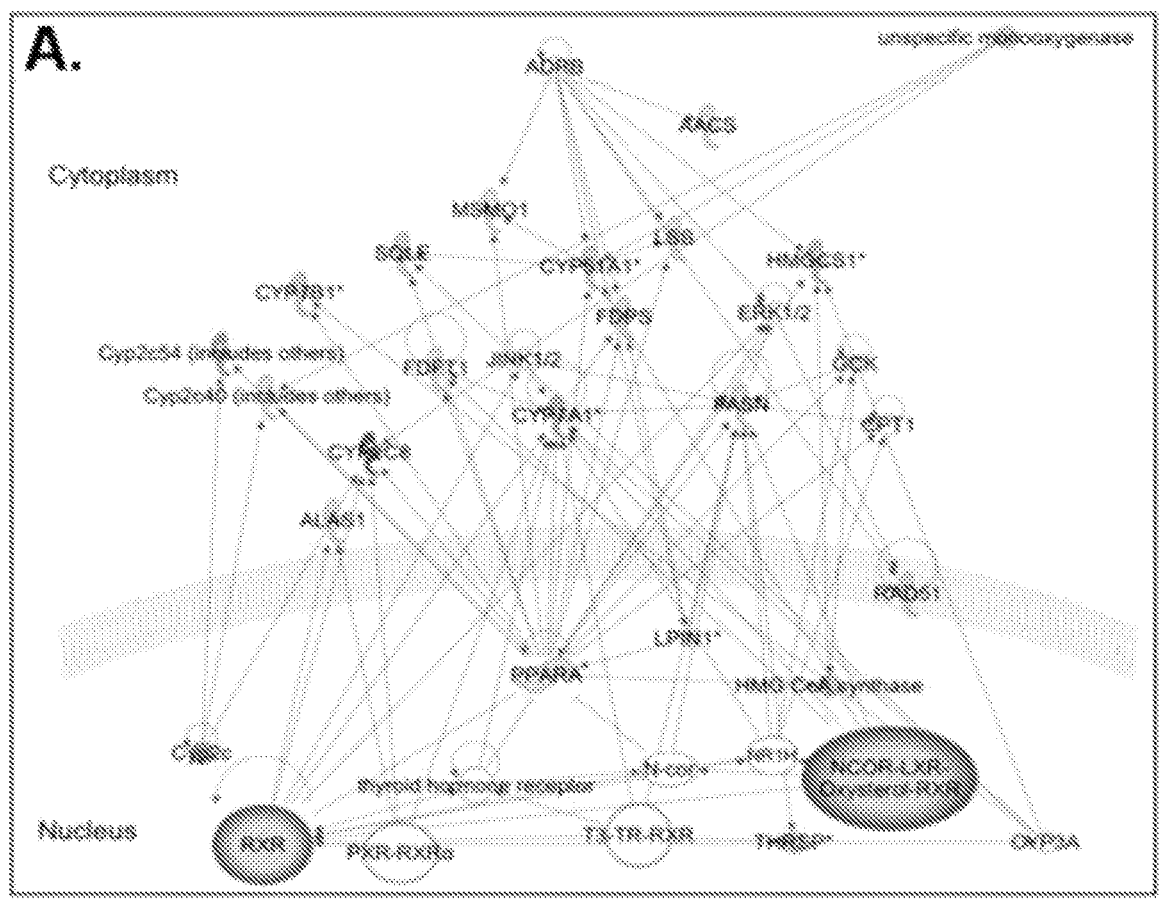
FIG. 1A-1C. Metabolic pathways affected in WD patients. Gene expression microarrays were performed on patients with WD and controls. Data was analyzed by GeneSifter and Ingenuity® software, which assigned altered transcripts to known metabolic and signaling pathways, and ranked the affected pathways based on the number of altered genes compared to a total number genes associated with the pathway.
Figure 1B:
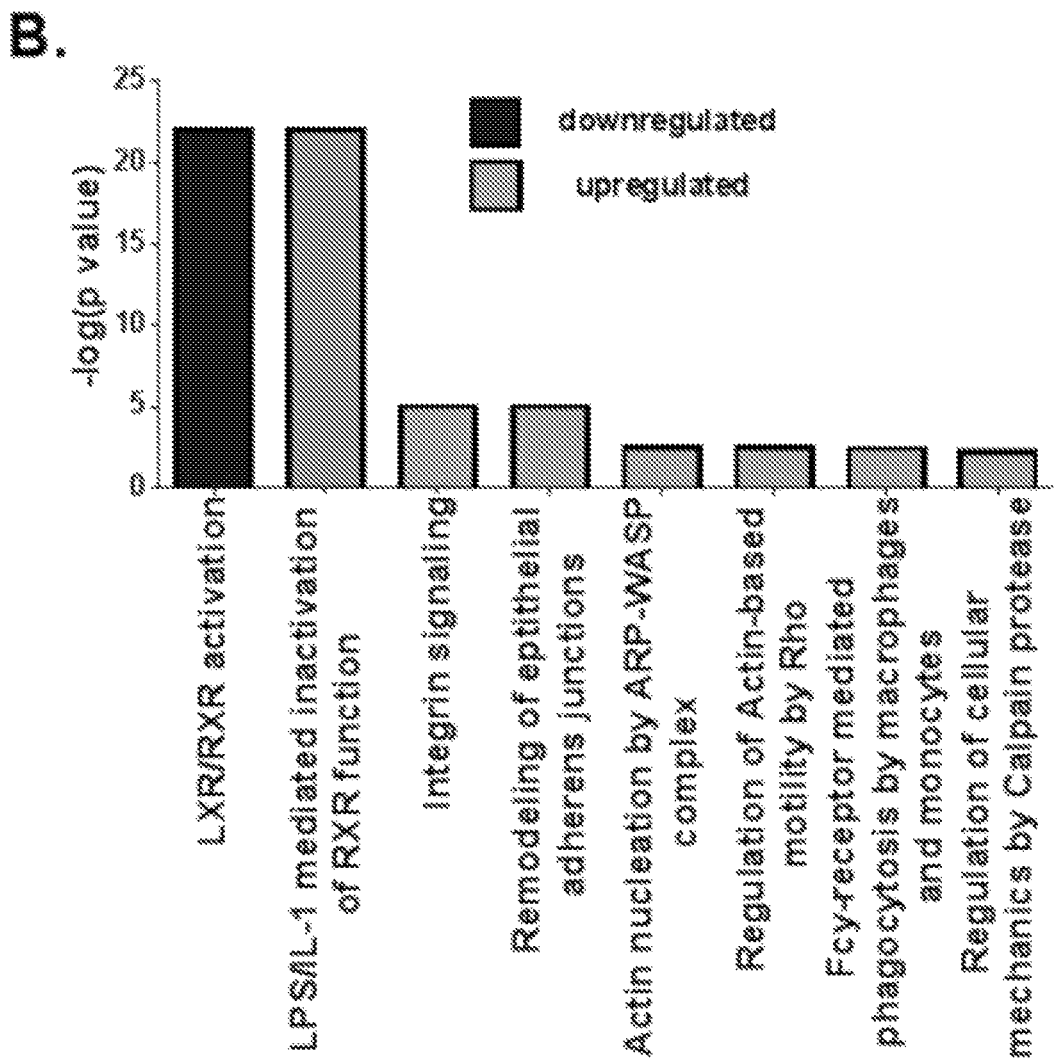
Figure 1C:
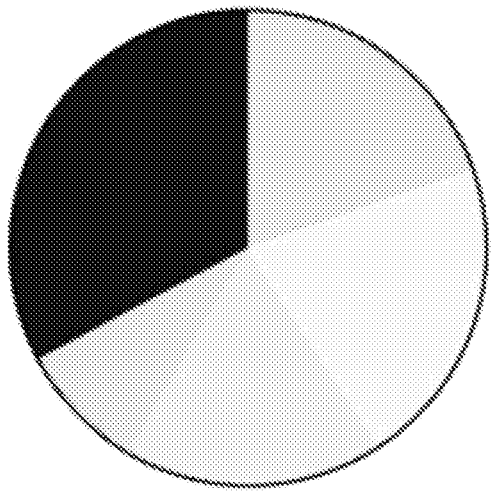

Lipid metabolism is abnormal in WD patients. Lipid metabolism in Atp7b$^{-/-}$ mice is significantly affected by copper overload, even before liver disease is detected. The mRNA profiling and pathway analysis suggests that down-regulation of cholesterol biosynthesis is due to inhibition of signaling by nuclear receptors, especially the LXR/RXR heterodimer (FIG. 1A). To examine relevance of these observations to human WD, we performed mRNA profiling of liver explants from 6 WD patients (2 samples did not pass quality control standards) using microarrays, and compared the profiles to those from 8 control individuals. All WD livers were at the advanced stage of disease, which produced changes in a large number of biological processes and pathways. The pathways most affected were LXR/RXR activation (downregulated) and IL-1β inactivation of RXR (upregulated) (FIG. 1B). Changes in lipid and carbohydrate metabolism represent the largest fraction of metabolic changes (32.76%) with lipid metabolism responsible for most of these changes (24%) (FIG. 1C) The most significant change was down-regulation of signaling mediated by the FXR/RXR or LXR/RXR nuclear receptors ($^{47}/_{116}$ genes affected, p=2.28×10$^{-22}$, FIGS. 1B and C Taken together, the in silico analysis of gene expression indicated that LXR/RXR mediated regulation of lipid metabolism was the most affected pathway in patients with WD and Atp7b$^{-/-}$ mice, and therefore a promising target for further investigation.

Figure 2A:
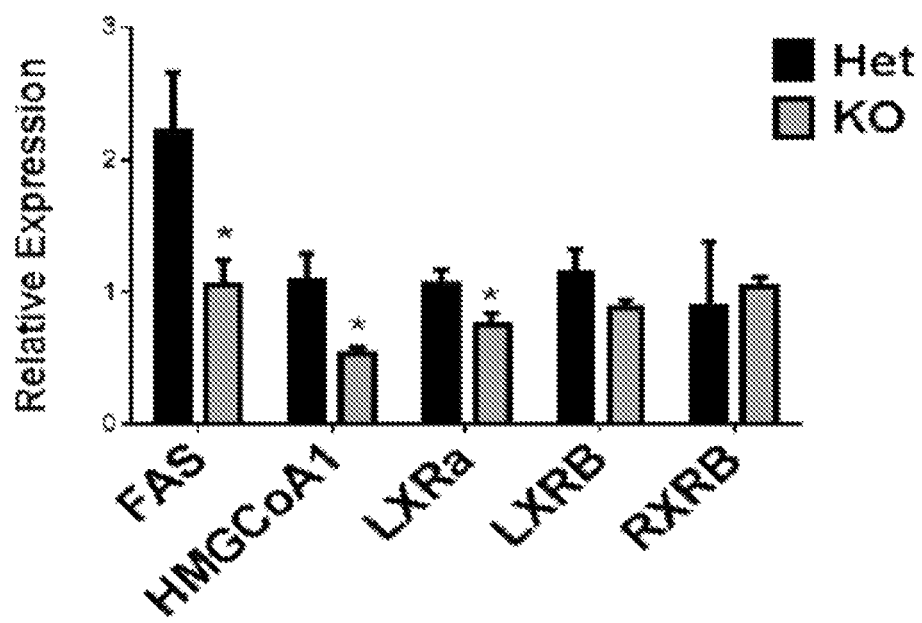
FIG. 2A-2C. The LXR/RXR program is down regulated in ATP7B KO mice.
Figure 2B:
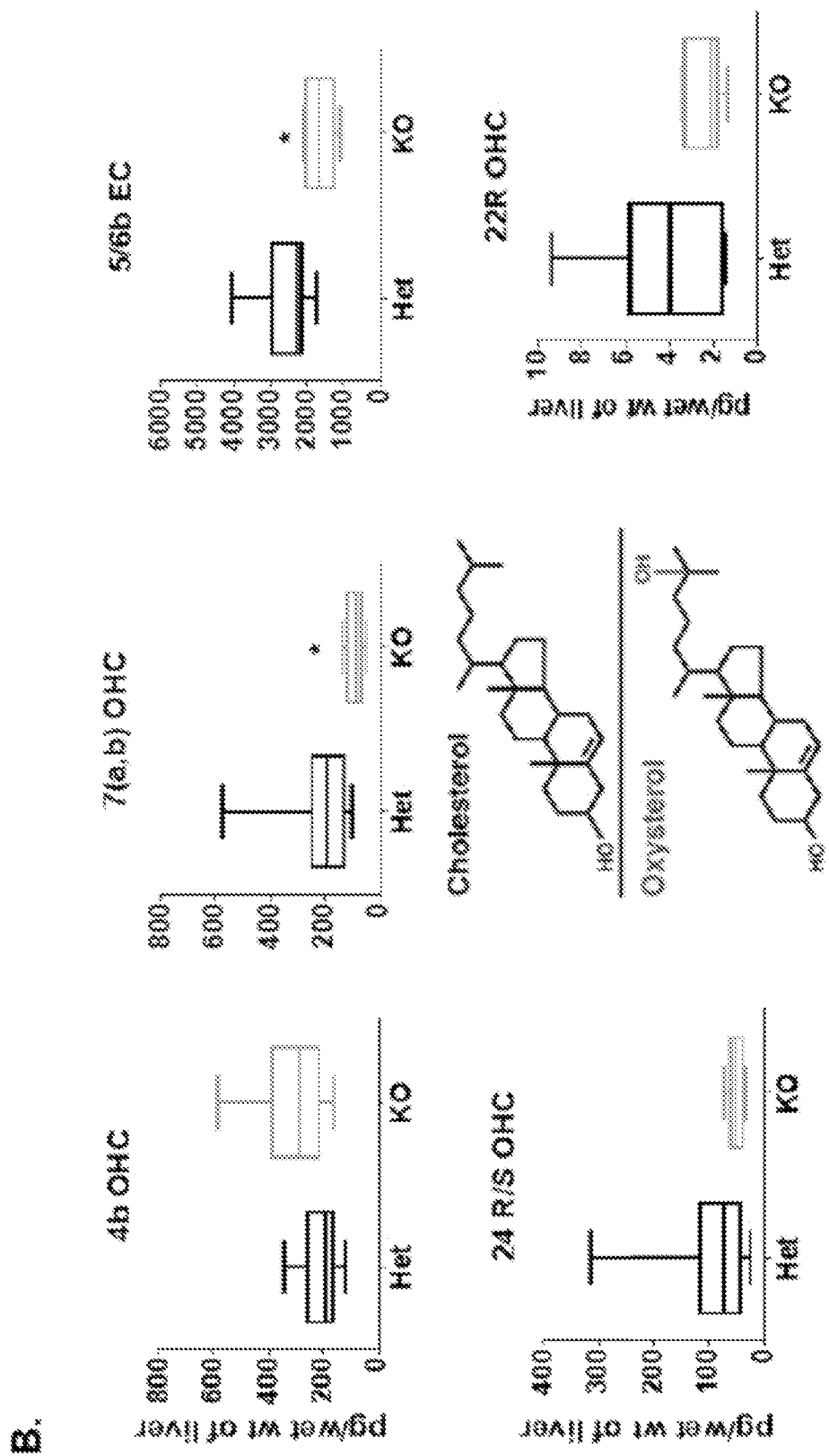

The level of RXR nuclear receptor and LXR/RXR targets are decreased in Atp7b$^{-/-}$ mice. The functional status of LXR/RXR pair was evaluated by measuring expression levels of LXR/RXR targets—fatty acid synthase and HMG-CoA reductase. The mRNA levels for both genes were significantly down-regulated in Atp7b$^{-/-}$ livers consistent with lower LXR/RXR activity (FIG. 2A). The apparently diminished LXR/RXR function could be either due to decreased levels of endogenous activating ligands, or due to lower expression of these receptors. Oxysterols (OHC) are potent activators of LXR. Mass-spectrometry analysis of OHC profiles demonstrated that the mean levels of LXR ligands 24S-OHC and 22R-OHC were lower in Atp7b$^{-/-}$ mice compared to control, however the decrease was not statistically significant. Statistically significant decreases were observed for 7α,β-OHC (produced by the FXR target Cyp7a1) and 5,6β-epoxycholesterol (5,6β-EC). By comparison, the levels of 4β-hydroxycholesterol were higher in Atp7b$^{-/-}$ mice compared to control (FIG. 2B); this OHC is a marker of activation of CYP3A4/5, which is regulated primarily by constitutive androstane receptor (CAR)-mediated signaling, rather than LXR.

Since the decrease in LXR ligands was modest, we also examined abundance of LXRα, LXRβ and RXR. LXRα mRNA (NR1H3) was decreased in the Atp7b$^{-/-}$ liver, whereas protein levels were not changed significantly. There was no difference in LXRβ (NR1H2) or RXRβ (NR2B2) mRNA (FIG. 2A) and protein levels of LXRβ were only slightly decreased.

Figure 2C:
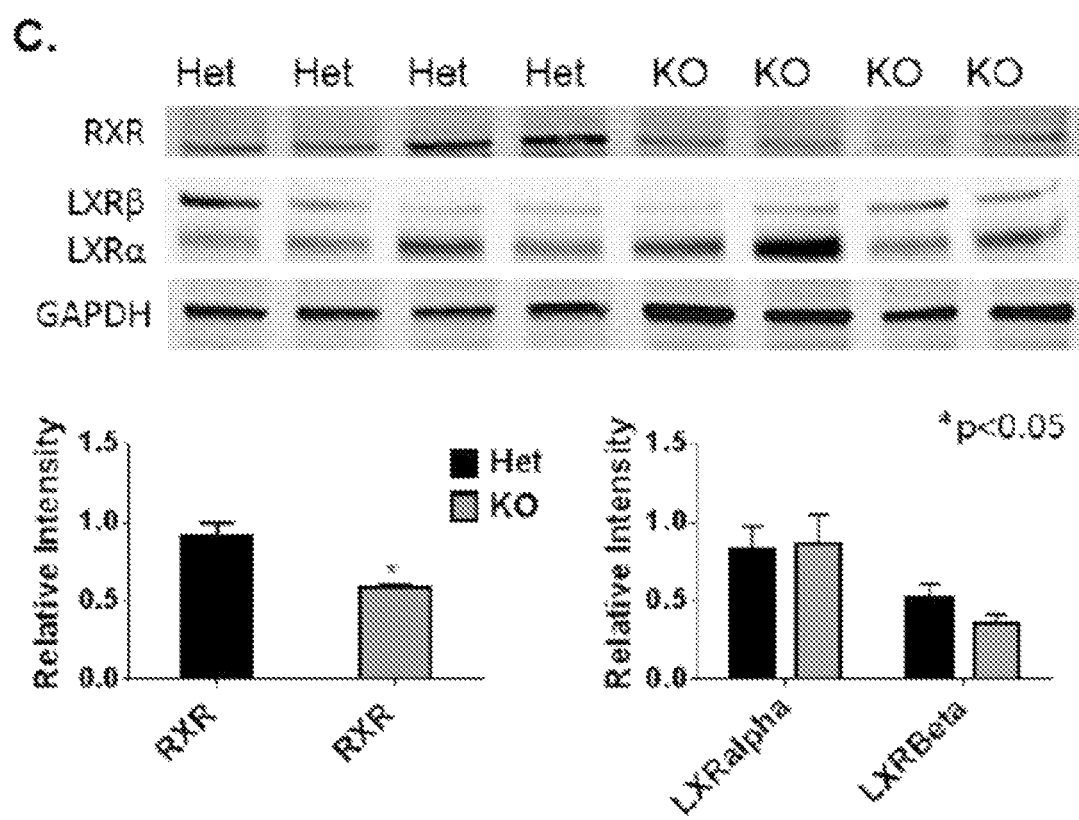

In contrast, RXR was significantly less abundant in both the cytoplasmic and nuclear fractions from the Atb7b$^{-/-}$ liver (FIG. 2C and FIG. 7). Thus, lower expression of LXR/RXR-regulated genes could be due to decreased RXR and a reduced number of functional LXR/RXR dimers. Oxidative stress is known to stimulate the phosphorylation of ERK1/2, p38 MAPK, and SAPK/JNK, which represses RXR expression and signaling. However, we did not find evidence of increased phosphorylation of these proteins (data not shown).

Treatment with LXR agonist T0901317 does not prevent copper accumulation in the liver. Activation of LXR/RXR upregulates lipid metabolism and inhibits inflammatory response. We hypothesized that reductions in LXR/RXR function may be responsible for the inhibition of cholesterol biosynthesis and increased hepatic inflammation observed in WD patients and Atp7b–/– mice, and play an important role in the development of liver pathology in WD. If true, activation of the LXR/RXR pathway may prevent hepatitis and improve liver function. To test this hypothesis, we examined the effect of an LXR agonist (T0901317) on copper levels, lipid metabolism, liver morphology and function in Atp7b$^{-/-}$ mice (KO). The histologically and biochemically normal heterozygote (HET) mice were used as controls.

The HET animals that received the drug were significantly heavier than the age-matched controls (26.43±1.35 g vs. 22.53±0.72 g, p<0.05, FIG. 8A), whereas there was neither a difference in the body weights (24.03±0.91 g vs. 24.67±1.54) nor the liver weights between the treated and untreated KO animals (FIG. 8B). Copper overload is the initial metabolic trigger for development of liver pathology in WD and it was important to determine that the drug acts down-stream of copper by activating lipid metabolism and not by diminishing copper levels in tissue. At the end of the experiment, copper levels in the KO mice were increased 38-fold compared to HET control. Similar increase was observed in drug-treated Atp7b$^{-/-}$ mice (FIG. 3A), indicating that T0901317 did not prevent copper accumulation.

T0901317 normalizes lipid metabolism in Atp7b$^{-/-}$ mice by upregulating expression of a subset of the LXR target genes. LXR is a transcription factor for multiple genes that regulate cholesterol synthesis, transport and metabolism. In the untreated Atp7b$^{-/-}$ mice, in addition to fatty acid synthase (FASN), and 3-hydroxyl-3-methylglutaryl-CoA synthase 1 (HMGCS1), the expression of NR1H4, and cytochrome P450 family 7 subfamily A polypeptide 1 (CYP7A1) was significantly lower compared to the untreated controls, whereas transcripts for ATP-binding cassette 1 (ABC1) and Sterol regulatory element-binding protein 1 (SREBP1) were not significantly different. Treatment with T0901317 significantly increased the FASN expression in both Atp7b$^{+/-}$ mice and Atp7b$^{-/-}$ mice. SREBP1 mRNA was increased in the ATP7b$^{+/-}$ mice after the treatment, but there was no change in the ATP7b$^{-/-}$ mice. In both KO and HET mice, the treatment did not change mRNA levels for NR1H2, NR1H3, NR1H4, ABC1, HMGCS1, or CYP7A1 (FIG. 9).

Figures 3A, 3B, 3C:
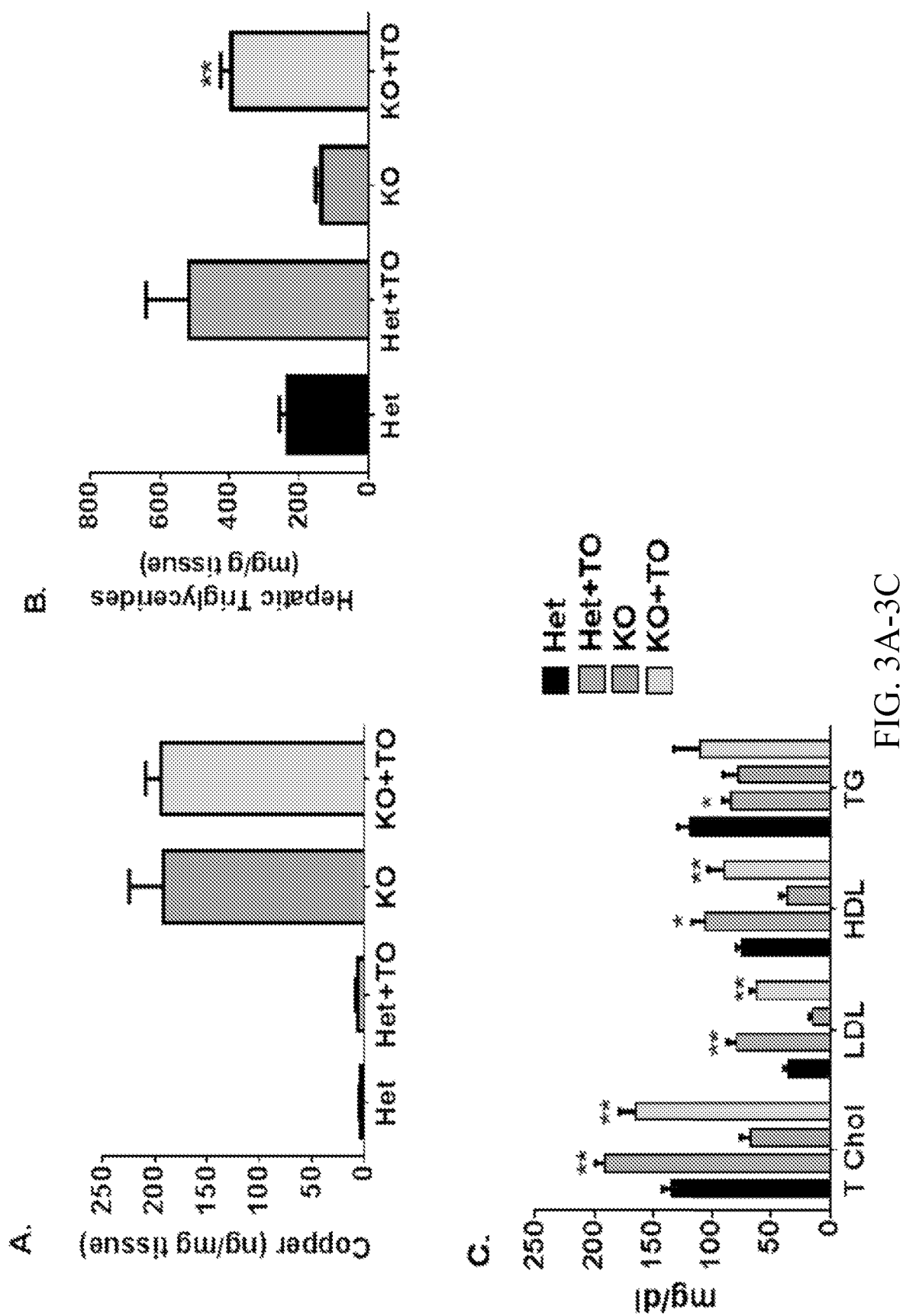
FIG. 3A-3C. Effect of the LXR agonist. There was no effect on Hepatic copper levels, which remained high in the ATP7B KO mice (FIG. 3A). The hepatic triglyceride content was significantly increased in the mice treated with the LXR agonist (FIG. 3B). Serum lipids were elevated in the treated mice (FIG. 3C). Statistical comparisons were made between untreated and treated mice of the same genotype (e.g. KO v KO+TO; *$p<0.05$, **$p<0.0005$; Abbreviations: TO: TO901317).

The mixed mRNA response to T0901317 indicated that only a subset of predicted targets of LXR/RXR pathway was stimulated by the drug. RXR dimerizes with other nuclear receptors (FIG. 1a), so the observed partial correction of transcriptional changes could be due to contributions from other RXR-dependent pathways. Given this partial response, we directly tested whether treatment with T0901317 reversed changes in lipid metabolism. The livers of both the drug treated HET and KO mice showed a statistically significant increase in triglycerides compared to the respective untreated controls (FIG. 3B), which was expected for treatment with T0901317. Plasma lipid analysis revealed that total cholesterol, low density lipoprotein (LDL), and high density lipoprotein (HDL) levels were all significantly increased in the sera of the drug treated Atp7b$^{-/-}$ mice compared to untreated Atp7b$^{-/-}$ mice (p<0.001, p<0.001, and p<0.005, respectively). Importantly, although the total cholesterol, LDL, and HDL more than doubled in the treated Atp7b$^{-/-}$ mice compared to the untreated mice, these resulting levels were similar to treated and untreated heterozygote mice (FIG. 3C, 3D). Collectively, the increases in hepatic triglycerides and serum lipids in the treated mice are consistent with activation of LXR/RXR signaling.

Treatment with T0901317 Decreases Inflammation and Liver Fibrosis in Atp7b$^{-/-}$ Liver.

Figures 4A, 4B, 4C, 4D:
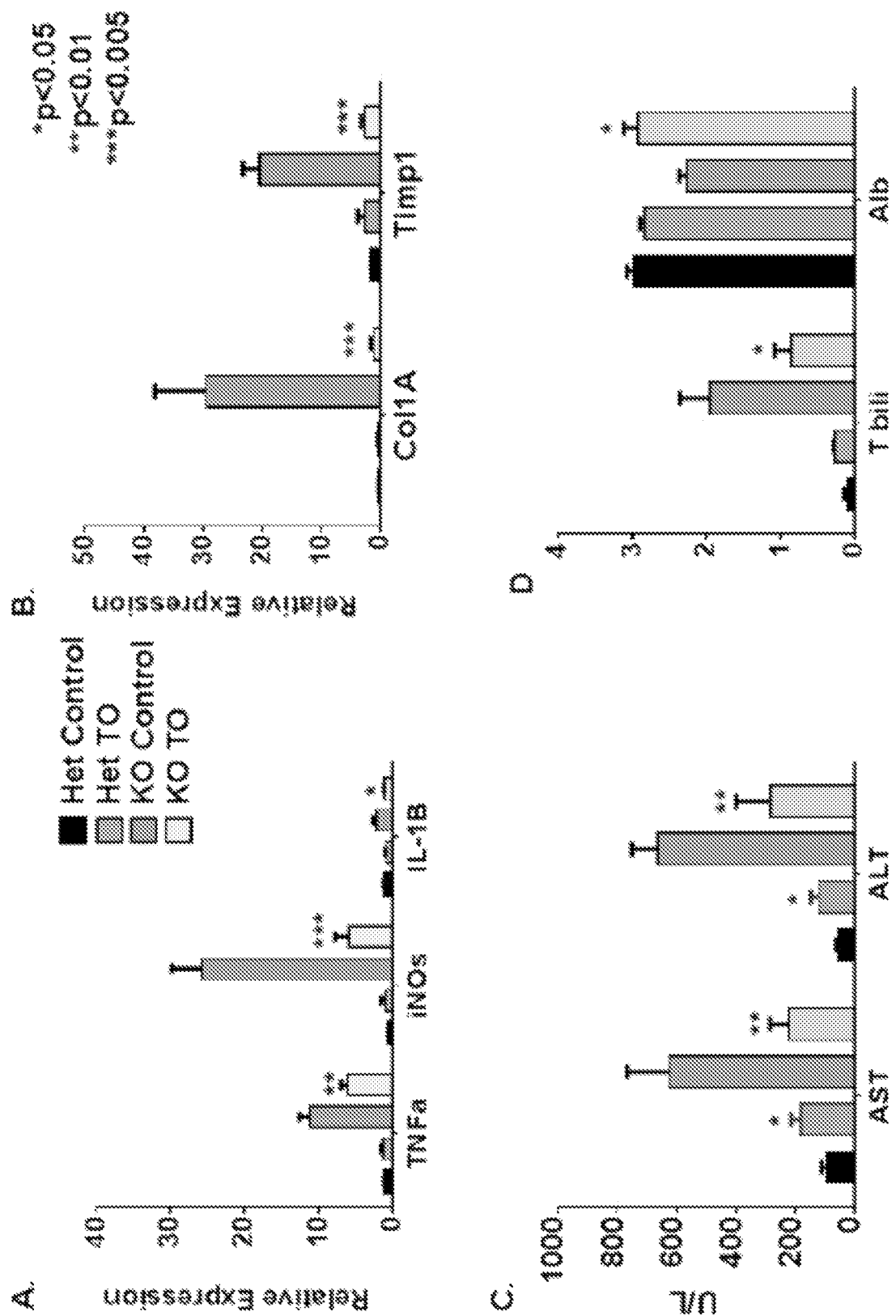
FIG. 4A-4D. LXR agonist reduces inflammatory and fibrosis genes, reduces liver enzymes, and improves liver function. Significant reductions in the mRNA expression of inflammatory genes (FIG. 4A) and liver fibrosis genes (FIG. 4B) were found in the KO mice treated with the LXR agonist. Serum AST, ALT (FIG. 4C) total bilirubin and albumin (FIG. 4D) significantly improved in the treated KO mice. Statistical comparisons were made between untreated and treated mice of the same genotype (e.g. KO v KO+TO; *$p<0.05$, $p<0.01$, *$p<0.005$).

Chronic inflammation underlies the development of liver fibrosis and ultimately, cirrhosis. Inactivation of LXR/RXR is expected to relieve inhibition of expression of genes associated with the NF-Kappa-B inflammatory cascade, whereas treatment with LXR/RXR agonist would facilitate inhibition. Indeed, untreated Atp7b$^{-/-}$ mice had a 10-fold increase in TNFα, a 2-fold increase IL-1β, and a 25-fold increase in iNOs expression when compared to the controls. Treatment with T0901317 significantly reduced the expression of these genes in the Atp7b$^{-/-}$ mice (FIG. 4A). There was no effect of drug treatment in the heterozygote animals.

Inflammatory cytokines TNFα and IL-1β activate hepatic stellate cells to produce collagen 1a, leading to fibrosis. The Atp7b$^{-/-}$ mice have a more than 25-fold increase of Col1a mRNA compared to the control mice. This increase in expression of collagen was completely abolished by treatment with T0901317 (FIG. 4B). Similarly, Tissue inhibitor of metalloproteinase 1 (Timp-1), a marker of inflammatory/fibrotic liver disease, was 20-fold higher in the untreated Atp7b$^{-/-}$ mice and similar to control following treatment with the drug (FIG. 4B).

LXR Agonist Improves Liver Function.

Aspartate aminotransferase (AST) and alanine aminotransferase (ALT) are enzymes elevated in the sera during liver inflammation and injury. In Atp7b$^{-/-}$ mice, the AST levels were 626±142 U/L and ALT was 666±85 U/L. Treatment with T0901317 significantly reduced the liver transaminases compared to untreated Atp7b$^{-/-}$ mice (p<0.05). The mean AST was reduced to 222±64 U/L and ALT to 285±115 U/L. The liver enzymes in the drug treated KO mice were similar to treated and untreated heterozygote mice (FIG. 4C). Liver function was further assessed by serum bilirubin and albumin levels. In treated Atp7b$^{-/-}$ mice the total bilirubin was significantly than in the untreated Atb7b$^{-1}$ mice (0.85±0.22 mg/dL vs. 1.96±0.39 mg/dL, p<0.05). Similarly, treatment improved the albumin levels to 2.93±0.19 mg/dL vs. 2.27±0.09 mg/dL in the untreated, knockout mice (p<0.05). (FIG. 4D).

Figures 5A, 5B:
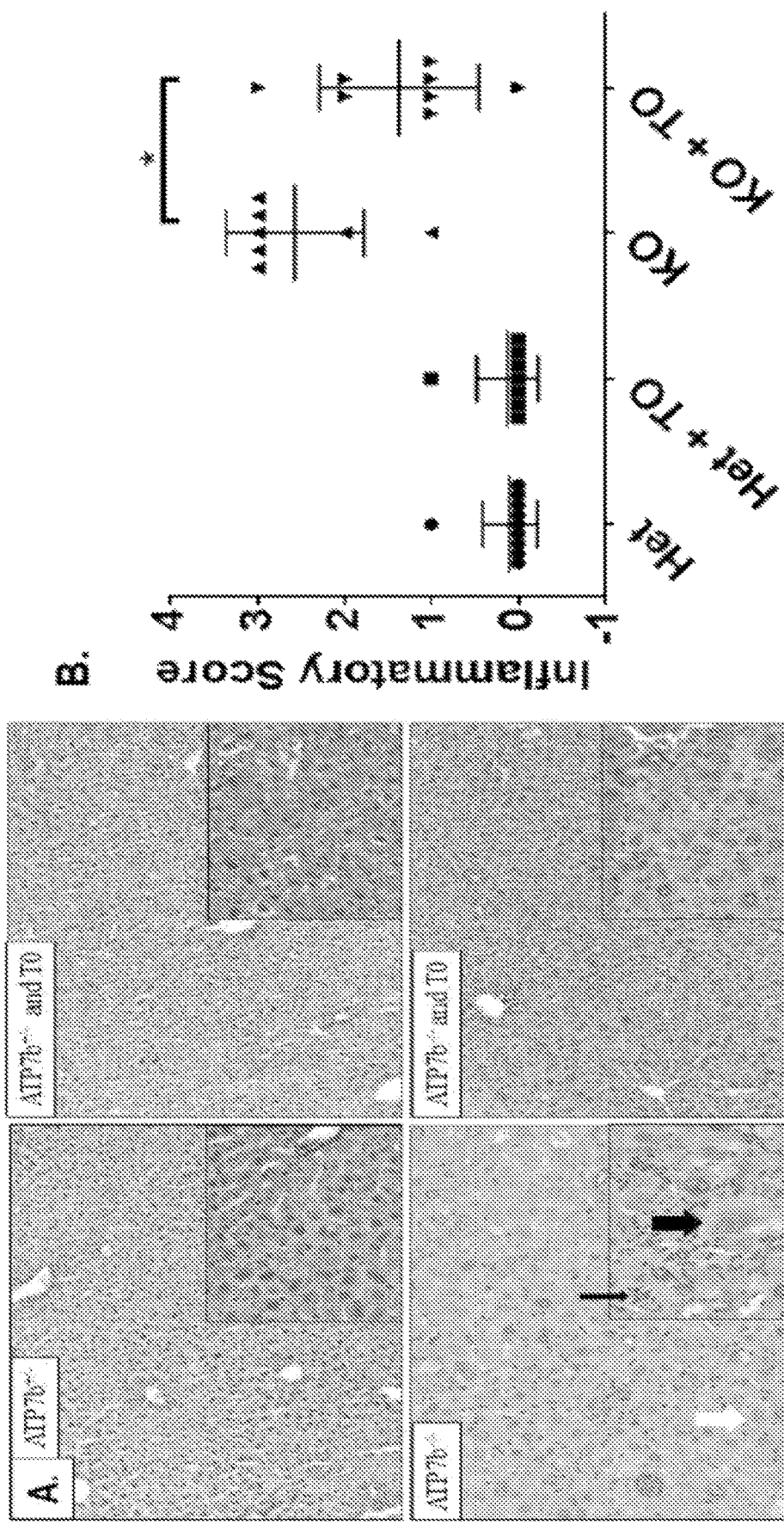
FIG. 5A-5B. LXR agonist improves liver histology and inflammation in ATP7b$^{-/-}$ mice. Representative hematoxylin and eosin stained liver sections from control and ATP7b$^{-/-}$ mice (FIG. 5A, 20×, inset 40×). Inflammation was scored as 0=none, 1=mild, 2=moderate, and 3=severe (FIG. 5B).

Liver histology was examined by light microscopy and confirmed significant improvements in the drug treated KO mice. Untreated KO mice livers have ballooning hepatocytes, intracytoplasmic vacuoles, karyomegaly, multiple nuclei, and inflammatory cell infiltrates. These pathologic features disappeared in 5/7 treated KO mice (FIGS. 5A and 5B). The treatment had no effect on the liver histology in the heterozygote mice.

Altogether, our findings are summarized in FIG. 6. The results suggest copper accumulation caused by inactivation of Atp7b is associated with inhibition of nuclear receptor signaling, especially, but not exclusively, the LXR/RXR heterodimer. We propose that the combined effects of reduced LXR/RXR activity in hepatocytes, stellate cells, and Kupffer cells all contribute to the pathogenesis of WD. Activation of this pathway with an endogenous agonist improved liver inflammation, histology, and liver function but did not alter hepatic copper.

Discussion

We demonstrate that the genetic program governing lipid metabolism and cholesterol biosynthesis is down-regulated in patients with Wilson disease and in Atp7b knockout mice. The change in transcriptional profiles is associated with decreased levels of cholesterol and triglycerides in serum and increased liver inflammation. In silico analysis linking gene expression to signaling pathways and metabolic processes pointed to inhibition of nuclear receptors in both mice and man as a primary cause of the observed changes. Consistent with this prediction, stimulation of nuclear receptor activity using the LXR agonist, T0901317, abrogated the major negative consequences of copper overload and improved liver morphology and function. Significantly, in the presence of the drug, the liver function was maintained (or had less decompensation) for a prolonged period of time despite elevated hepatic copper. We propose that in WD, accumulating copper inhibits nuclear receptor signaling, which is a critical mediator of liver injury in WD. This represents a novel mechanism in the pathogenesis of WD.

Copper chelation is an established and by in large successful approach to decreasing copper toxicity in WD. Life-long treatment using copper chelators improves liver function, but also has a wide range of side effects. Reaching a delicate copper balance in different tissues is difficult and prolonged chelation frequently produces neurologic decompensation and has other unintended consequences. Targeting pathways downstream of copper offers an alternative strategy for improving liver function in WD, especially under circumstances when copper chelators are ineffective or poorly tolerated. At the current stage, our data represent "a proof of concept" that stimulating nuclear receptor function can greatly diminish pathologic changes in WD liver. In this study, we initiated treatment with the drug when copper was high, lipid profile was altered, and AST/ALT were elevated, but the structural morphology of liver was still preserved, and we obtained very promising results. Whether similar treatment will be equally effective if started at a more advanced stage of the disease needs to be determined. It is likely that treatment combining mild copper chelation and activation of nuclear receptor signaling could be most effective.

Inflammation, lipid dis-homeostasis eventually leading to steatosis, and fibrosis are commonly observed in WD. Many of the genes regulating these processes are under the control of nuclear receptors, including the LXR/RXR heterodimer. The LXRα and LXRβ levels were unchanged in the KO mice, whereas RXR levels were lower in the KO mice. A lower abundance of RXR is likely to decrease transcriptional activity of the LXR/RXR heterodimer, although this remains to be formally demonstrated. Interestingly, IL-1β expression transiently stimulates SAPK/JNK resulting in RXR export from the nucleus, followed by proteosomal degradation. IL-1β is elevated in the WD mice, suggesting a possible explanation for diminished protein levels of RXR. Another factor potentially contributing to lower abundance/activity of RXR are levels of endogenous ligands. Oxysterols regulate activity of the LXR/RXR dimer, and the oxysterol profile differed significantly between the control and knockout animals. In particular, 7α,β-OHC and 5,6β-EC levels were significantly lower in the knockout animals compared to healthy controls, whereas 4β-OHC was increased in the ATP7b deficient mice. Treatment with the drug did not reverse changes in oxysterol levels (not shown), indicating that that the cause for oxysterol misbalance was upstream (or produced independently) of LXR/RXR signaling. Such causes may involve copper dependent, non-enzymatic oxidation and/or inhibition of activity of enzymes involved in oxysterol metabolism.

The LXR agonist used in this study had an uneven effect on gene expression. Genes commonly associated with liver fibrosis (COL1a and TIMP1) and liver inflammation (TNFα, IL-1β, and iNOS) were dramatically down-regulated by the treatment in knockout animals, suggesting primary control by LXR. At the same time, only a sub-set of genes involved in lipid metabolism responded to treatment with the drug. This result indicates that the decrease in RXR may have a negative effect on the function of several receptors involved in lipid metabolism with which RXR dimerizes, such as FXR, PPAR, and RAR. Despite partial recovery of mRNA levels, serum lipids in the treated mice increased to levels similar to those found in control mice. In addition, hepatic triglyceride content was increased in the treated mice, strongly suggesting the recovery of LXR signaling in the treated Atb7b$^{-/-}$ mice.

Our findings of reduced Col1A, and TIMP-1 in treated Atb7b$^{-/-}$ mice corroborate previous studies that indicate LXR activation in hepatic stellate cells is a critical determinant of liver inflammation and fibrosis. LXRα/β-/- mice have an exaggerated inflammatory and fibrotic response to classic experimental hepatic insults. Furthermore, bone marrow transplants between wild type and LXRα/β-/- mice had no effect on the severity of fibrosis, suggesting the LXR signaling in hepatic stellate cells and/or hepatocytes is critical for the development of hepatic fibrosis. Future studies are needed to test the effects of ATP7b deletion, copper overload, and NR function in specific cell types in the liver.

Treatment of hepatoblastoma cells (HepG2) with copper induces apoptosis that is mediated by an increase in acid sphingomeylinase (ASMase) activity and production of ceramide. ASMase activity is increased by TNFα and ASMase deficiency renders cultured hepatocytes resistant to TNFα mediated apoptosis. We observed high levels of TNFα mRNA in liver extracts from the Atp7b KO mice, and the LXR agonist dramatically reduced the TNFα. Analysis of sphingolipids in one KO animal and age-matched control showed increased levels of ceramide, although separate study is needed to determine significance of this pathway in mice and humans. Elevated levels of serum TNFα and IL-1β are found in patients with WD (as in our mouse model).

In conclusion, treatment with an LXR agonist improved liver histology, liver enzymes and liver function in a mouse model of WD. The improvements were associated with a decrease in genetic markers of liver fibrosis and inflammatory cytokines. There was no change in hepatic copper. These findings suggest alterations in nuclear receptor mediated lipid metabolism and inflammation may contribute to the pathogenesis of liver disease in WD, and that alternative therapies targeting these receptors, which augment or even replace copper chelation are possible.

We claim:

1. A method for treating a patient suffering from Wilson Disease comprising the step of administering to the patient an effective amount of a liver X receptor (LXR) agonist.

2. The method of claim 1, wherein the LXR agonist is a natural oxysterol, a synthetic oxysterol, a synthetic nonoxysterol or a natural nonoxysterol.

3. The method of claim 1, wherein the LXR agonist is 20(S) hydroxycholesterol, 22(R) hydroxycholesterol, 24(S) hydroxycholesterol, 25-hydroxycholesterol, 24(S), 25 epoxycholesterol, 27-hydroxycholesterol, N,N-dimethyl-3β-hydroxycholenamide, N-(2,2,2-trifluoroethyl)-N-{4-[2,2,2-trifluoro-1-hydroxy-1 (trifluoromethyl)ethyl]phenyl}benzene sulfonamide, [3-(3-(2-chloro-trifluoromethylbenzyl-2,2-diphenylethylamino)propoxy) phenylacetic acid], N-methyl-N-[4-(2,2,2-trifluoro-1-hydroxy-1-trifluoromethyl-1-ethyl)phenyl]-benzenesulfonamide, 4,5-dihydro-1-(3-(3-trifluoromethyl-7-propyl-benzisoxazol-6-yloxy)propyl)-2,6-pyrimidinedione, 3-chloro-4-(3-(7-propyl-3-trifluoromethyl-6-(4,5)-isoxazolyl)propylthio)-phenyl acetic acid, acetyl-podocarpic dimer, paxilline, desmosterol, or stigmasterol.

4. The method of claim 3, wherein the LXR agonist is N-(2,2,2-trifluoroethyl)-N-{4-[2,2,2-trifluoro-1-hydroxy-1-(trifluoromethyl)ethyl]phenyl}benzene sulfonamide.

5. The method of claim 1, wherein the LXR agonist is 22(R)-hydroxycholesterol, 24(S)-hydroxycholesterol, 27-hydroxycholesterol, or cholestenoic acid.

6. The method of claim 1, wherein the LXR agonist is hypocholamide, T0901317, GW3965, or N,N-dimethyl-3beta-hydroxy-cholenamide (DMHCA).

7. A pharmaceutical composition comprising an LXR agonist and a copper chelator.

8. The composition of claim 7, wherein the copper chelator is penicillamine, bathocuproine sulfonate, sodium diethyldithiocarbamate, trientine hydrochloride, or dimercaprol.

9. The composition of claim 7, wherein the copper chelator is penicillamine or tientine hydrochloride.

10. A pharmaceutical composition comprising an LXR agonist and a metallothionein inducer.

11. The composition of claim 10, wherein the metallothionein inducer is a zinc salt.

12. The composition of claim 11, wherein the zine salt is zinc acetate.

13. A pharmaceutical composition comprising an LXR agonist and zine acetate.

14. A pharmaceutical composition comprising an LXR agonist, a copper chelator and a metallothionein inducer.

15. A pharmaceutical composition comprising an LXR agonist, a copper chelator and zinc acetate.

16. The method of claim 1, further comprising administering to the patient an effective amount of a copper chelator.

17. The method of claim 16, wherein the copper chelator is penicillamine, bathocuproine sulfonate, sodium diethyldithiocarbamate, trientine hydrochloride, dimercaprol or zinc acetate.

18. The method of claim 16, wherein the copper chelator is penicillamine or tientine hydrochloride.

19. The method of claim 16, further comprising administering to the patient an effective amount of a metallothionein inducer.

* * * * *

UNITED STATES PATENT AND TRADEMARK OFFICE
CERTIFICATE OF CORRECTION

PATENT NO. : 10,583,102 B2
APPLICATION NO. : 15/517197
DATED : March 10, 2020
INVENTOR(S) : Svetlana Lutsenko and James Hamilton Page 1 of 1

It is certified that error appears in the above-identified patent and that said Letters Patent is hereby corrected as shown below:

In the Specification

Column 1 Line 15 replace the second paragraph as follows:
STATEMENT OF GOVERNMENTAL INTEREST
This invention was made with government support under DK117396, awarded by the National Institutes of Health. The government has certain rights in the invention.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*